US012648766B2

(12) United States Patent
Prusener et al.

(10) Patent No.: US 12,648,766 B2
(45) Date of Patent: Jun. 9, 2026

(54) DEVICES, SYSTEMS, AND METHODS FOR TREATING VESSEL WALL OPENINGS

(71) Applicant: Medtronic, Inc., Minneapolis, MN (US)

(72) Inventors: Derek W. Prusener, St. Louis Park, MN (US); Jonathan E. Baxter, Fridley, MN (US); Kevin R. Seifert, Forest Lake, MN (US); Mikayle A Holm, St. Anthony, MN (US)

(73) Assignee: Medtronic, Inc., Minneapolis, MN (US)

( * ) Notice: Subject to any disclaimer, the term of this patent is extended or adjusted under 35 U.S.C. 154(b) by 104 days.

(21) Appl. No.: 18/627,729

(22) Filed: Apr. 5, 2024

(65) Prior Publication Data

US 2024/0358359 A1 Oct. 31, 2024

Related U.S. Application Data

(60) Provisional application No. 63/498,940, filed on Apr. 28, 2023.

(51) Int. Cl.
A61B 17/00 (2006.01)

(52) U.S. Cl.
CPC .................. *A61B 17/00491* (2013.01); *A61B 2017/00004* (2013.01); *A61B 2017/00367* (2013.01); *A61B 2017/00601* (2013.01); *A61B 2017/0065* (2013.01); *A61B 2017/00884* (2013.01);
(Continued)

(58) Field of Classification Search
CPC ...... A61B 2017/0065; A61B 17/00491; A61B 17/0057; A61B 17/12186; A61B 2017/00637; A61B 2017/00654; A61B 2017/00575; A61B 2017/00601; A61B 2017/0061; A61B 2017/00623;
(Continued)

(56) References Cited

U.S. PATENT DOCUMENTS 5,320,639 A * 6/1994 Rudnick ............... A61L 31/044
                                                      606/228
5,665,107 A 9/1997 Hammerslag
(Continued)

FOREIGN PATENT DOCUMENTS

WO 2009101505 A2 8/2009

*Primary Examiner* — Katherine H Schwiker
(74) *Attorney, Agent, or Firm* — Fortem IP LLP

(57) ABSTRACT

Devices, systems, and methods for treating vessel openings are disclosed herein. According to some embodiments, a device for treating a vessel opening comprises a housing configured to be positioned within an opening in subcutaneous tissue proximate the vessel opening. The housing can comprise an inner wall and an outer wall. The inner wall can define a first lumen configured to receive an elongate member therein and the inner and outer walls can define a second lumen configured to receive an adhesive. The outer wall of the housing can define one or more apertures extending radially from the second lumen to an environment external of the housing. The device can comprise an actuator configured to be received within the second lumen. Movement of the actuator can force the adhesive to move through the aperture to the external environment and into an extravascular space within the subcutaneous tissue proximate the vessel opening.

20 Claims, 11 Drawing Sheets

(52) U.S. Cl.
   CPC .............. *A61B 2017/00889* (2013.01); *A61B 2017/00893* (2013.01); *A61B 2017/00951* (2013.01)

(58) Field of Classification Search
   CPC ........... A61B 2017/00641; A61B 2017/00626; A61B 2017/00659; A61B 2017/00646
   See application file for complete search history.

(56) References Cited

U.S. PATENT DOCUMENTS

| | | | |
|---|---|---|---|
| 5,725,551 A * | 3/1998 | Myers ................ | A61B 17/0057 606/1 |
| 7,621,936 B2 * | 11/2009 | Cragg ................ | A61B 17/0057 604/15 |
| 2002/0026159 A1 | 2/2002 | Zhu et al. | |
| 2007/0149999 A1 * | 6/2007 | Szabo ................ | A61B 17/0057 606/214 |
| 2012/0221062 A1 * | 8/2012 | Wenger .............. | A61B 17/8822 606/304 |
| 2013/0238019 A1 | 9/2013 | Michlitsch | |
| 2014/0135824 A1 | 5/2014 | Terwey et al. | |
| 2015/0209019 A1 | 7/2015 | Yassinzadeh | |
| 2016/0113636 A1 | 4/2016 | Pipenhagen et al. | |
| 2016/0129220 A1 | 5/2016 | Jagadeesan et al. | |
| 2021/0060308 A1 | 3/2021 | Willard et al. | |

* cited by examiner

1

DEVICES, SYSTEMS, AND METHODS FOR TREATING VESSEL WALL OPENINGS

RELATED APPLICATIONS

This application claims the benefit of U.S. Provisional Application Ser. No. 63/498,940, filed Apr. 28, 2023, the entire contents of each of which are incorporated herein by reference.

TECHNICAL FIELD

The present technology relates generally to tissue puncture closure devices, and more particularly, to devices and methods for delivery of bioadhesive materials to a tissue puncture.

BACKGROUND

Traditionally, cardiovascular procedures have been performed as open surgical procedures in which one or more large incisions are made through the patient's skin to visualize the treatment site. Open cardiac surgical procedures further require cutting through the patient's breastbone and spreading the patient's ribcage to access the heart. More recently, transcatheter procedures have been developed that inflict significantly less trauma on the patient's body. Transcatheter procedures involve percutaneously accessing a blood vessel through a patient's skin and inserting a catheter into the lumen of the blood vessel. The catheter can be navigated through the patient's vasculature to deliver a medical device to a treatment site within the cardiovascular system. As one example, a distal end of the catheter can be navigated into the patient's heart and a leadless pacemaker can be delivered through the catheter into the patient's heart. In some procedures, such as balloon angioplasty, for example, the catheter itself can perform the medical intervention. In any case, by accessing the patient's vascular system with a small puncture or incision through the patient's skin, transcatheter procedures are less invasive, safer, and more efficient than open surgical procedures.

Upon completion of a transcatheter procedure, the catheter is removed from the patient's vasculature, leaving an opening in the wall of the blood vessel and the subcutaneous tissue through which the vessel was accessed. The opening allows blood to exit the vessel and presents a risk of bleeding. Thus, a need exists for devices and methods to close vessel openings and/or to prevent bleeding through vessel openings created during transcatheter procedures.

SUMMARY

The subject technology is illustrated, for example, according to various aspects described below, including with reference to FIGS. 1-10B. Various examples of aspects of the subject technology are described as numbered clauses (1, 2, 3, etc.) for convenience. These are provided as examples and do not limit the subject technology.

1. A device for delivering a medical adhesive to a subcutaneous region proximate and extravascular to an opening in a wall of a blood vessel, the device comprising:
   a housing comprising a proximal end and a distal end opposite the proximal end along a longitudinal dimension of the housing, the housing comprising:
   an inner wall and an outer wall extending along the longitudinal dimension of the housing, the outer wall radially spaced apart from and circumferentially surrounding the inner wall, wherein:
   the inner wall defines a first lumen extending from the proximal end of the housing to the distal end of the housing along the longitudinal dimension of the housing, the first lumen being open at the proximal and distal ends of the housing, wherein the first lumen is configured to receive an elongate member therein;
   a second lumen defined between the outer wall and the inner wall such that the second lumen at least partially circumferentially surrounds the first lumen and extends from the proximal end of the housing towards the distal end of the housing along the longitudinal dimension of the housing, the second lumen being open at the proximal end of the housing; and
   the outer wall defines an aperture extending radially through the outer wall from the second lumen to an environment external of the housing such that the aperture fluidically couples the second lumen to the environment external of the housing;
   a medical adhesive positioned within the second lumen of the housing; and
   an actuator configured to be slidably received within the second lumen, wherein movement of the actuator within the second lumen forces the medical adhesive to move through the aperture to the environment external of the housing.

2. The device of Clause 1, wherein the actuator comprises a proximal end and a distal end opposite the proximal end along a longitudinal dimension of the actuator, the actuator comprising a sidewall defining a channel extending longitudinally from the proximal end of the actuator to the distal end of the actuator, wherein the channel is open at the proximal and distal ends of the actuator and is configured to receive the elongate member therein.

3. The device of Clause 2, wherein, when the actuator is positioned within the second lumen, the channel at least partially circumferentially surrounds the first lumen.

4. The device of any one of Clauses 1 to 3, wherein at least a distal end of the actuator has an outer diameter at least as large as an outer diameter of the second lumen.

5. The device of any one of Clauses 1 to 4, wherein distal advancement of the actuator relative to the housing forces the medical adhesive to move through the aperture to the environment external of the housing.

6. The device of any one of Clauses 1 to 5, wherein proximal retraction of the actuator relative to the housing forces the medical adhesive to move through the aperture to the environment external of the housing.

7. The device of any one of Clauses 1 to 6, wherein sliding the actuator longitudinally relative to the housing forces the medical adhesive to longitudinally align with and move through the aperture to the environment external of the housing.

8. The device of Clause 7, wherein prior to longitudinally sliding the actuator relative to the housing, the medical adhesive does not longitudinally align with the aperture.

9. The device of any one of Clauses 1 to 8, wherein the actuator includes a shaft and a plunger distal of the shaft, the plunger having a proximal flange, a distal flange opposite the proximal flange along a longitudinal dimension of the plunger, and an intermediate wall therebetween, and wherein the proximal and distal flanges each have an outer diameter at least as large as an outer diameter of the second lumen and the intermediate wall has an outer diameter less than the outer diameter of the proximal and distal flanges.

10. The device of Clause 9, wherein the proximal and distal flanges and the intermediate wall of the actuator define a chamber region, and wherein, when the actuator is positioned within the second lumen, the medical adhesive is positioned within the chamber region within the second lumen radially between the intermediate wall and the housing.

11. The device of Clause 9 or Clause 10, wherein the actuator comprises a rib extending longitudinally within the chamber region such that, when the actuator is positioned within the second lumen, the rib extends radially from the intermediate wall of the actuator to the housing.

12. The device of Clause 11, wherein rotation of the actuator relative to the housing causes the rib to force the medical adhesive to move circumferentially through the second lumen and radially through the aperture to the environment external of the housing.

13. The device of Clause 12, wherein rotating the actuator relative to the housing causes the rib to force the medical adhesive to circumferentially align with the aperture.

14. The device of Clause 13, wherein, prior to rotating the actuator relative to the housing, the medical adhesive does not circumferentially align with the aperture.

15. The device of any one of Clauses 11 to 14, wherein the rib is a first rib, the actuator further comprising a second rib extending longitudinally within the chamber region, the second rib being circumferentially spaced apart from the first rib.

16. The device of Clause 15, wherein, when the actuator is positioned within the second lumen, the medical adhesive is located circumferentially between the first and second ribs.

17. The device of Clause 15 or Clause 16, wherein rotating the actuator relative to the housing causes at least one of the first rib or the second rib to force the medical adhesive to circumferentially align with the aperture.

18. The device of Clause 17, wherein, prior to rotating the actuator relative to the housing, the medical adhesive does not circumferentially align with the aperture.

19. The device of any one of the preceding Clauses, wherein the outer wall of the housing defines a plurality of apertures.

20 The device of Clause 20, wherein at least some of the apertures are at least partially longitudinally aligned.

21 The device of Clause 20 or Clause 21, wherein at least some of the apertures are at least partially circumferentially aligned.

22. The device of any one of the preceding Clauses, wherein the outer wall of the housing tapers in a distal direction.

23. The device of any one of the preceding Clauses, wherein an outer diameter of the housing is greater at the proximal end portion of the housing than at the distal end portion of the housing and/or an intermediate portion of the housing.

24. The device of any one of the preceding Clauses, wherein an outer diameter of the actuator is greater at the proximal end portion of the actuator than at the distal end portion of the actuator and/or an intermediate portion of the actuator.

25. The device of any one of the preceding Clauses, wherein the second lumen is closed at the distal end of the housing.

26. A method of treating an opening in a wall of a blood vessel of a patient, the method comprising:
positioning a distal end portion of an elongate member within a lumen of the blood vessel and positioning a proximal end portion of the elongate member external to the patient's skin such that an intermediate portion of the elongate member extends from the distal end portion to the proximal end portion through a vessel opening defined by the vessel wall and through a tissue opening defined by subcutaneous tissue proximate to and extravascular of the vessel opening;
positioning the proximal end portion of the elongate member within a first lumen defined by an inner wall of a housing and distally advancing the housing into the tissue opening over the elongate member until a distal end portion of the housing is proximate to and extravascular of the vessel opening, wherein the housing comprises an outer wall and the outer and inner walls together define a second lumen at least partially circumferentially surrounding the first lumen, the second lumen retaining an adhesive therein;
positioning an actuator within the second lumen; and
moving the actuator within the second lumen to force the adhesive to move through an aperture extending radially through the outer wall of the housing from the second lumen to the tissue opening such that the adhesive adheres to the subcutaneous tissue.

27. The method of Clause 26, wherein moving the actuator comprises distally advancing the actuator.

28 The method of Clause 26 or Clause 27, wherein moving the actuator comprises proximally retracting the actuator.

29 The method of any one of Clauses 26 to 28, wherein moving the actuator comprises rotating the actuator.

30. The method of any one of Clauses 26 to 29, wherein moving the actuator forces the adhesive to longitudinally align with the aperture.

31. The method of any one of Clauses 26 to 30, wherein moving the actuator forces the adhesive to circumferentially align with the aperture.

32. The method of any one of Clauses 26 to 31, wherein moving the actuator increases a pressure within the second lumen.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

The present technology relates to devices, systems, and methods for closing openings in blood vessels. Some embodiments of the present technology, for example, are directed to devices, systems, and methods for delivering an adhesive to an extravascular space proximate an opening in a wall of a blood vessel. The adhesive can be used to adhere together portions of the subcutaneous tissue circumferentially surrounding and defining the tissue opening to effectively seal the vessel opening and prevent or limit blood flow through the vessel opening.

Figures 1, 2:
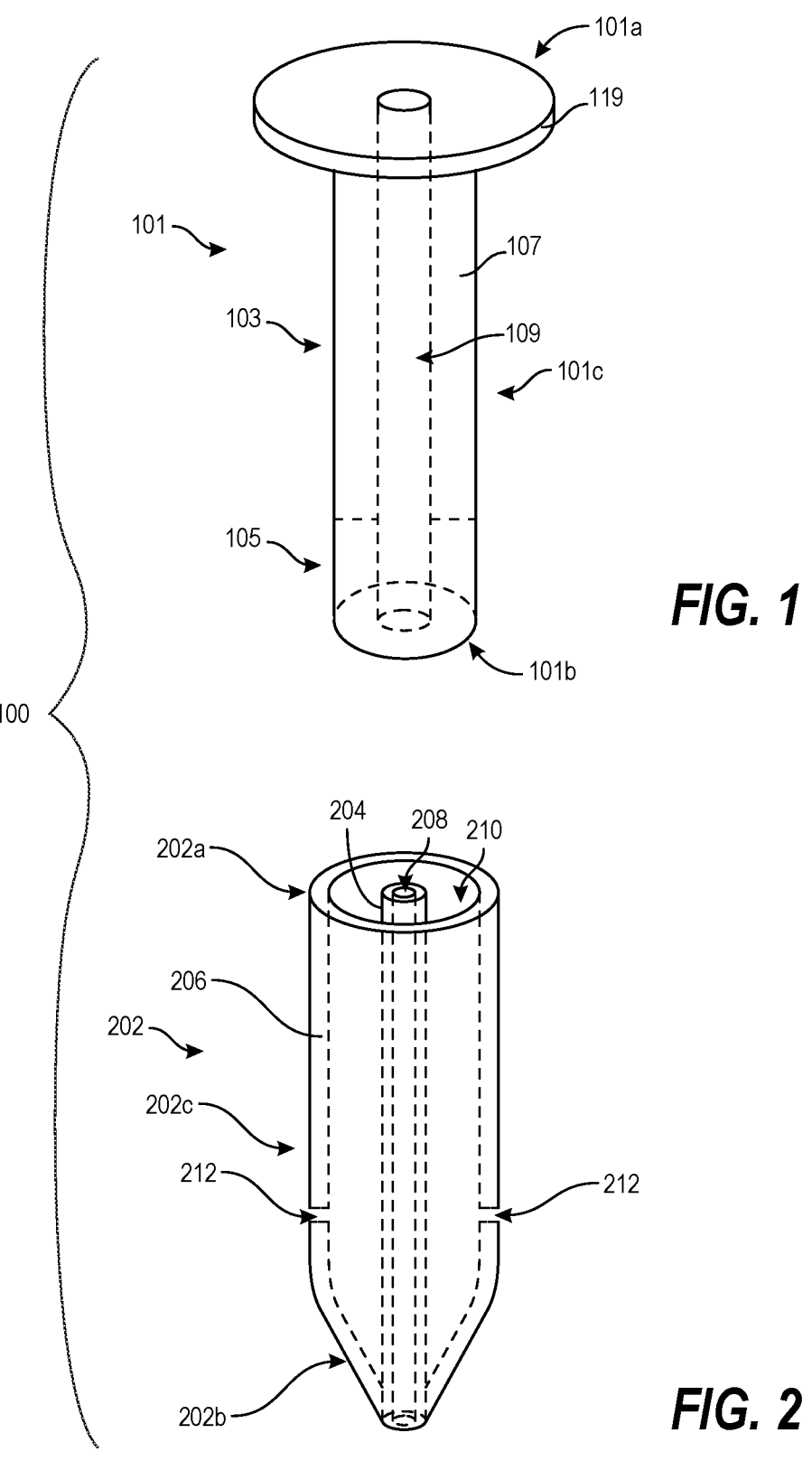
FIG. 1 illustrates an actuator of an adhesive delivery device in accordance with several embodiments of the present technology.
FIG. 2 illustrates a housing of the adhesive delivery device of FIG. 1 in accordance with several embodiments of the present technology.

FIGS. 1 and 2 illustrate components of an adhesive delivery device 100 (or "device 100") in accordance with various embodiments of the present technology. The adhesive delivery device 100 can comprise an actuator 101 (FIG. 1) and a housing 202 (FIG. 2). As detailed below, the actuator 101 is configured to be positioned within an interior region of the housing 202 and moved within the interior region to expel adhesive from a distal portion of the housing 202.

As shown in FIG. 1, the actuator 101 includes a proximal end portion 101a, a distal end portion 101b opposite the proximal end portion 101a along a longitudinal dimension of the actuator 101, and an intermediate portion 101c between the proximal and distal end portions 101a, 101b. The actuator 101 can comprise a shaft 103 and a plunger 105 disposed at the distal end of the shaft 103. The shaft 103 and/or plunger 105 can be defined by an annular sidewall 107 that partially or completely circumferentially surrounds a channel 109. For example, the shaft 103 and/or plunger 105 can have an annular ring shape. The shaft 103 and the plunger 105 may comprise a monolithic structure or may comprise components formed separately and later coupled together via mechanical fastening, welding, adhesive, etc. In some embodiments, for example as shown in FIG. 1, the proximal end portion 101a of the actuator 101 includes a projection 119 that is wider than the shaft 103 and is configured to facilitate grasping and/or manipulating the actuator 101 and/or to provide a mechanical stop to limit distal advancement of the actuator 101 relative to the housing 202. The projection 119 can be monolithic with the shaft 103 or can comprise a distinct component formed separately from and later coupled to the shaft 103 (e.g., via mechanical fastening, welding, adhesive, etc.).

As shown in FIG. 2, the housing 202 of the adhesive delivery device 100 includes a proximal end portion 202a, a distal end portion 202b opposite the proximal end portion 202a along a longitudinal dimension of the housing 202, and an intermediate portion 202c between the proximal and distal end portions 202a, 202b. The housing 202 can comprise a generally tubular inner wall 204 and a generally tubular outer wall 206 extending along the longitudinal dimension of the housing 202. The outer wall 206 can partially or completely circumferentially surround and be radially spaced apart from the inner wall 204. As shown in FIG. 2, in some embodiments the outer wall 206 tapers in a distal direction such that an outer diameter of the outer wall 206 decreases towards the distal end of the housing 202. Such distal tapering of the outer wall 206 can facilitate insertion of the housing 202 into an opening in the subcutaneous tissue of a patient. Still, in some embodiments the outer diameter of the outer wall 206 is substantially constant along a length of the housing 202 and/or a distal end of the housing 202 is blunt. Although not shown in FIG. 2, in some embodiments the proximal end portion 202a of the housing 200 can include a projection that is wider than the distal end portion 202b of the housing 202 and/or the intermediate portion 202c of the housing 202. Similar to projection 119, the projection of the housing 202 can be configured to facilitate grasping and/or manipulating the housing 202 and/or to provide a mechanical stop to limit distal advancement of the housing 202 into the patient's tissue.

The inner wall 204 can partially or completely circumferentially surround and define a first lumen 208 that extends longitudinally from an opening at the proximal end portion 202a of the housing 202 to an opening at the distal end portion 202b of the housing 202. The first lumen 208 can be configured to slidably receive an elongate member (e.g., a guidewire, a coil, a catheter, etc.) therein such that the housing 202 can be advanced over the elongate member into and through a patient's subcutaneous tissue. In some embodiments, a diameter of the first lumen 208 is at least as large as an outer diameter of the elongate member to be used with the adhesive delivery device 100.

Referring still to FIG. 2, the inner and outer walls 204, 206 of the housing 202 can define a second lumen 210 configured to receive at least a portion of the actuator 101 therein. The second lumen 210 can partially or completely circumferentially surround the first lumen 208. For example, as shown in FIG. 2, in some embodiments the second lumen 210 is circumferentially continuous and completely circumferentially surrounds the first lumen 208. Alternatively, the second lumen 210 can extend around a central angle of less than 360 degrees. In such embodiments, the sidewall 107 of the actuator 101 can extend around the same central angle as the second lumen 210 such that the sidewall 107 can be received within the second lumen 210. In some embodiments, the second lumen 210 is concentric and/or coaxial with the first lumen 208. In any case, the second lumen 210 extends longitudinally from the proximal end portion 202a of the housing 202 towards the distal end portion 202b. In some embodiments, the second lumen 210 is closed at the distal end of the housing 202. Alternatively, the second lumen 210 can be partially or completely open at the distal end of the housing 202.

The second lumen 210 can be configured to contain an adhesive. The outer wall 206 of the housing 202 can define one or more apertures 212 extending radially through the outer wall 206 from the second lumen 210 to an environment external of the housing 202. The apertures 212 can fluidically couple the second lumen 210 to the external environment to provide a passageway for adhesive to travel from the second lumen 210 to the external environment. Although FIG. 2 illustrates two apertures 212 circumferentially offset from and longitudinally aligned with one another, the housing 202 can comprise any suitable number, spacing, and/or sizing of apertures 212. For example, the housing 202 can comprise a plurality of apertures 212 that are at least partially spaced apart along the longitudinal dimension of the housing 202 and/or at least partially spaced apart around a circumferential dimension of the housing 202. In some embodiments, a size of the apertures 212 can increase or decrease along the longitudinal dimension and/or the circumferential dimension of the housing 202. The apertures 212 can be sufficiently large to permit movement of a high viscosity adhesive through the apertures 212. A device 200 configured for use with a lower viscosity adhesive may have smaller apertures 212 than a device 200 configured for use with a higher viscosity adhesive. The apertures 212 can be substantially circular or may have any suitable shape such as, but not limited to, quadrilateral, triangular, elliptical, polygonal, non-polygonal, etc. In some embodiments, the outer wall 206 of the housing 202 can be selectively permeable to the adhesive. For example, one or more portions of the outer wall 206 of the housing 202 can comprise a mesh defining a plurality of pores through which the adhesive can travel under certain conditions such as, but not limited to, an increase in pressure in the second lumen 210.

The actuator 101 can be configured to interact with the housing 202 to cause the adhesive to move through the apertures 212, thereby expelling the adhesive from the second lumen 210. To align the actuator 101 with the housing 202 and provide a continuous passageway for an elongate member to be positioned within, the channel 109 can be configured to receive the inner wall 204 of the housing 202 therein (e.g., a diameter of the channel 109 can be at least as large as an outer diameter of the inner wall 204). The inner wall 204 of the housing 202 and/or the first lumen 208 can be coaxial and/or concentric with the channel 109 when the inner wall 204 is received within the channel 109. Additionally, at least a portion of the actuator 101 can be configured to be received within the second lumen 210 of the housing 202. For example, at least the plunger 105 of the actuator 101 can be configured to be received within the second lumen 210 of the housing 202. In some embodiments, at least a portion of the shaft 103 of the actuator 101 is also configured to be received within the second lumen 210. An outer diameter of the second lumen 210 can be at least as large as a maximum outer diameter of the shaft 103 such that the shaft 103 is slidable through the second lumen 210. The sidewall 107 and/or the channel 109 of the actuator 101 can be coaxial and/or concentric with the second lumen 210, the first lumen 208, and/or the inner wall 204 when the actuator 101 is received within the second lumen 210. In general, movement of the shaft 103 and/or plunger 105 within the second lumen 210 causes the adhesive to move through the apertures 212 of the housing 202.

Figure 3A:
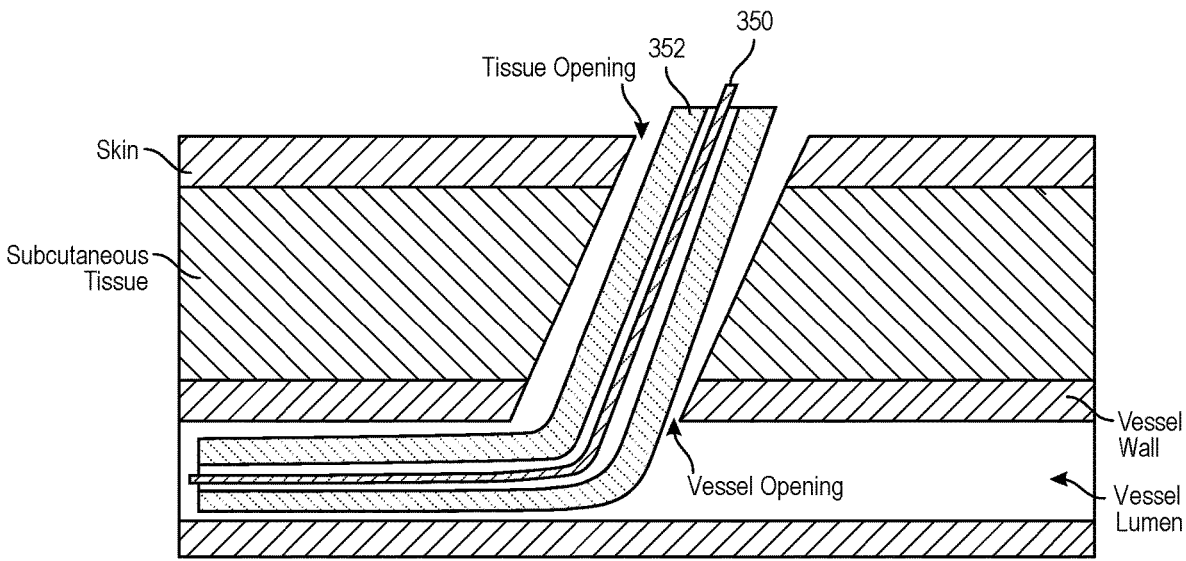
FIGS. 3A-3F show an example method of closing a vessel opening using the adhesive delivery devices of the present technology.

FIGS. 3A-3F illustrate an example method of closing an opening in a blood vessel (also referred to herein as a "vessel opening"), for example by operating the adhesive delivery device 100 of FIGS. 1 and 2. As shown in FIG. 3A, the vessel opening can be created during a percutaneous transcatheter procedure in which the vessel is accessed through the skin and subcutaneous tissue of a patient. During the procedure, a needle can be inserted through the skin, subcutaneous tissue, and vessel wall to provide access to the vessel lumen. The needle can be inserted into the skin and subcutaneous tissue at a non-perpendicular angle to the vessel. In some procedures, the vessel can be accessed via a cut-down procedure in which an incision is made through the patient's skin and subcutaneous tissue.

An elongate member 350 can be inserted through a lumen of the needle into the vessel lumen to provide and maintain access to the vessel lumen. The elongate member 350 can comprise a guidewire, a suture, a coil, a catheter, and/or another suitable structure for placement within the vessel lumen. The needle can be retracted proximally over the elongate member 350 and removed from the subcutaneous tissue and skin, leaving an opening in the subcutaneous tissue and skin (also referred to herein as a "tissue opening") surrounding the elongate member 350. One or more interventional members 352 can be inserted over the elongate member 350 and distally advanced over the elongate member into the vessel lumen via the tissue and vessel openings. The elongate member 350 can be positioned within a lumen of the interventional member 352 to guide the interventional member 352 into the vessel lumen. Insertion of the interventional member 352 into the tissue opening can increase a diameter of the tissue opening and/or one or more additional interventional members 352 can be advanced into the tissue opening prior to insertion of the interventional member 352 to increase a diameter of the tissue opening to accommodate the interventional member 352. The interventional member 352 can comprise a catheter, a dilator, an introducer, and/or any other suitable medical device. A distal end of the interventional member 352 can be navigated through the vessel lumen to a treatment site within the patient's cardiovascular system. The interventional member 352 can be configured to perform a medical procedure and/or one or more additional medical devices can be advanced through a lumen of the interventional member 352 into the patient's cardiovascular system. Such medical devices can comprise, for example, progressively smaller catheters, a delivery system, a treatment device, etc.

Figure 3B:
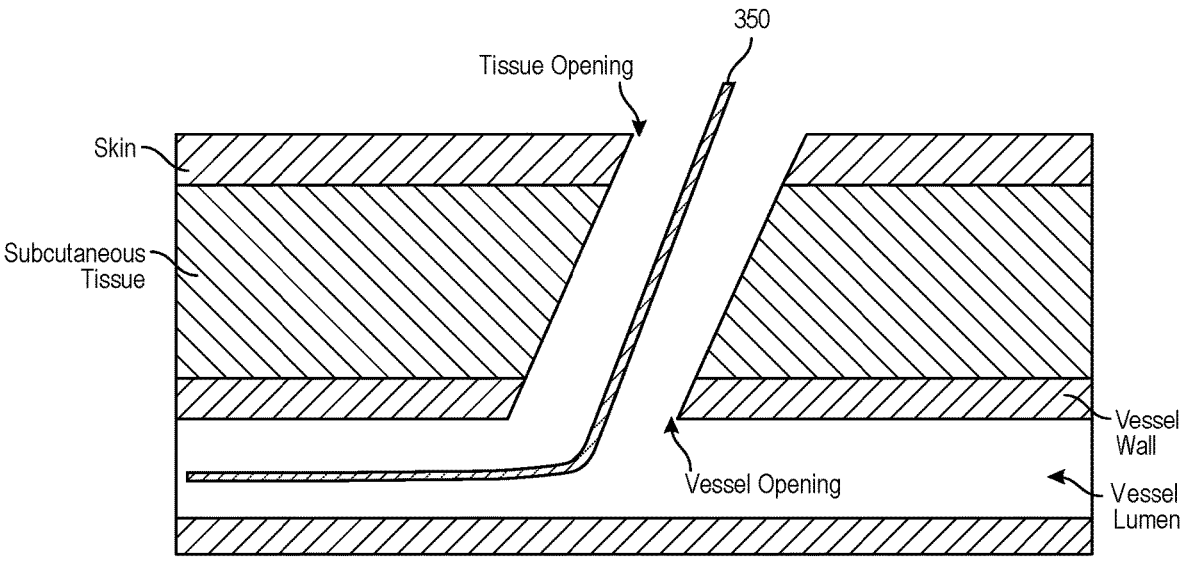
Figure 3C:
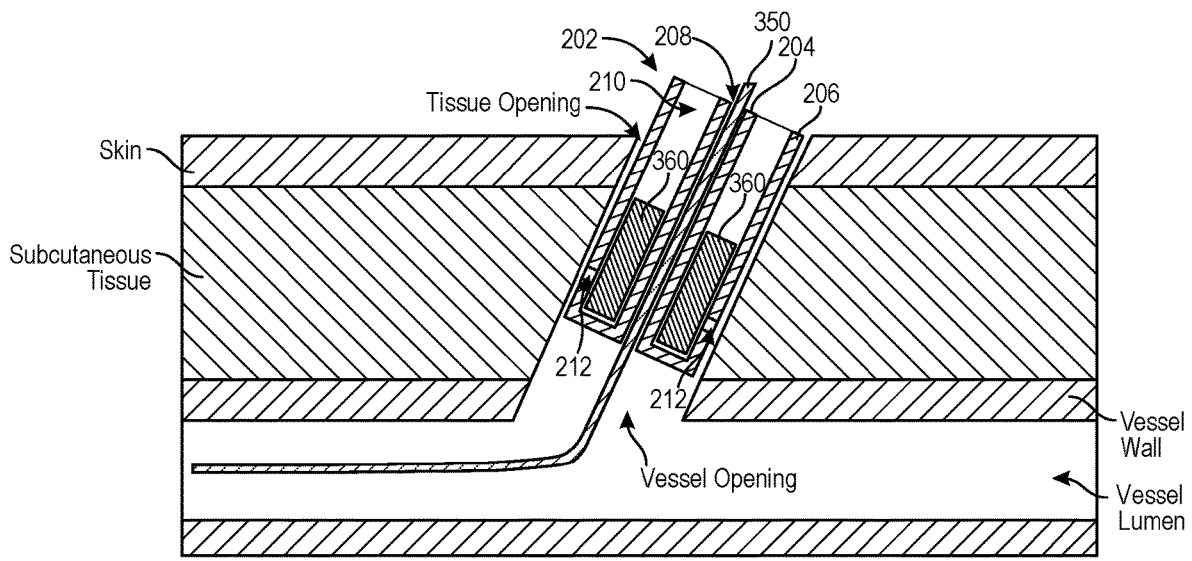

A medical procedure can be performed with the interventional member 352 and/or medical device(s). When the medical procedure is complete, the medical device(s) and/or interventional member 352 can be removed from the vessel lumen, the subcutaneous tissue, and the skin, thereby leaving a continuous opening between the vessel and the skin surface, as shown in FIG. 3B. In some embodiments the elongate member 350 can be retained within the vessel opening and/or the tissue opening after the interventional member 352 has been removed to maintain access to the vessel and tissue openings. The elongate member 350 can be used to guide the adhesive delivery device into an intended position proximate the vessel opening. For example, as shown in FIG. 3C, the elongate member 350 can be positioned within the first lumen 208 of the housing 202 and the housing 202 can be slidably advanced over the elongate member 350 into the tissue opening. The distal end of the housing 202 can be positioned proximate to the vessel wall and extravascular of the vessel opening. In some embodiments, the housing 202 can be advanced through the tissue opening until a distal end of the housing 202 contacts the vessel wall, thereby locating the distal end of the housing 202 proximate the vessel opening.

In some embodiments, an anchor can be delivered into the vessel lumen prior to, during, and/or after advancement of the housing 202 into the tissue opening. The anchor can be configured to transform from a constrained configuration for delivering through the tissue and vessel openings to an expanded configuration in which an outer radial dimension of the anchor is greater than a radial dimension of the vessel opening. The anchor can comprise any suitable expandable structure such as, but not limited to, an inflatable balloon, an expandable mesh, a coil, a footplate, and others. The anchor can be slidably advanceable over the elongate member and/or slidably advanceable through the first lumen 208 of the housing 202. The anchor can be positioned in contact with the luminal surface of the vessel wall so that the anchor extends across and blocks the vessel opening. The anchor can therefore prevent blood flow from the vessel lumen through the vessel opening. Moreover, the anchor can prevent adhesive from prolapsing from the tissue opening into the vessel lumen. In some embodiments, the anchor can be configured to prevent the housing 202 from being advanced into the vessel opening and/or the vessel lumen and can therefore be used to position the housing 202 within the tissue opening.

Although FIG. 3C illustrates the housing 202 as having a blunt distal end, as previously noted with reference to FIG. 2, the housing 202 may have a tapered distal end. In some embodiments, an outer diameter of the housing 202 can be greater than a diameter of the tissue opening. Thus, as the housing 202 is inserted into the tissue opening over the elongate member 350, the housing 202 can dilate the tissue opening and increase its diameter. Providing the housing 202 with a tapered distal end can facilitate dilating the tissue opening while preventing or limiting damage to the surrounding subcutaneous tissue.

Once the housing 202 is positioned within the tissue opening, the housing 202 can substantially block the vessel opening to prevent or limit blood flow through the vessel opening. Additionally or alternatively, an operator can apply pressure to the skin proximate to (e.g., upstream of, etc.) the vessel opening after removing the interventional member 352 and/or while inserting the housing 202 into the tissue opening to restrict blood flow to the vessel opening.

An adhesive 360 can be preloaded in the second lumen 210 prior to advancing the housing 202 into the tissue opening and/or the adhesive 360 can be advanced into and/or through the second lumen 210 after the housing 202 has been advanced into the tissue opening. In any case, the housing 202 can be configured to retain the adhesive 360 within the second lumen 210 until an operator intentionally expels the adhesive 360 from the second lumen 210. As previously noted, the second lumen 210 can be closed at the distal end of the housing 202 such that adhesive 360 will not be expelled in a distal direction from the housing 202 towards the vessel opening. Advantageously, the closed distal end of the second lumen 210 can prevent or limit adhesive 360 from being pushed into the vessel opening and/or the vessel lumen, which could obstruct the vessel lumen.

The adhesive 360 can comprise any suitable composition for facilitating adhesion of subcutaneous tissue to itself. Example adhesives 360 may include cyanoacrylate (e.g., 2-octyl cyanoacrylate). In some examples, a cyanoacrylate can be an aliphatic 2-cyanoacrylate ester such as an alkyl, cycloalkyl, alkenyl or alkoxyalkyl2-cyanoacrylate ester. The alkyl group may have from 1 to 16 carbon atoms in some embodiments, and can be a C1-C8 alkyl ester or a C1-C4 alkyl ester. Some possible esters include the methyl, ethyl, npropyl, isopropyl, n-butyl, isobutyl, pentyl, hexyl, cyclohexyl, heptyl, octyl, 2-methoxyethyl and 2-ethoxyethyl esters of cyanoacrylic acid. In some embodiments, the adhesive 360 comprises a n-butyl cyanoacrylate, such as VenaSeal™ adhesive, sold by Medtronic, Inc. Additional example adhesives 360 can include biological glue such as a bovine serum albumin-gluteraldehyde combination (e.g., BIOGLUE, Cryolife, Atlanta, Ga.), PV A, Biogard, collagen, fibrinogen, fibronectin, vitronectin, laminin, thrombin, gelatin, combinations thereof, or other biocompatible adhesives. In some examples, the adhesive 360 can also include a therapeutic agent such as a thrombogenic agent, an anti-inflammatory agent, an anti-infective agent, an anesthetic, a pro-inflammatory agent, a cell proliferative agent, or combinations thereof. The adhesive 360 can be bioabsorbable and/or biodegradable, according to some embodiments.

Figure 3D:
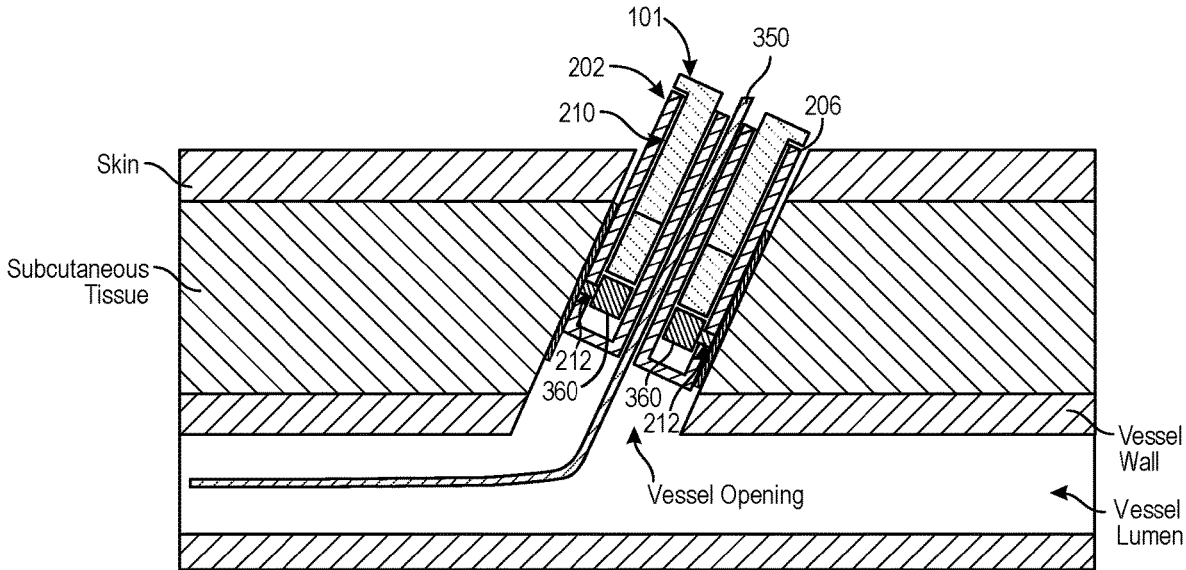

As shown in FIG. 3D, the adhesive 360 can be expelled from the second lumen 210 through the apertures 212 in the outer wall 206 of the housing 202. In some embodiments, for example as shown in FIG. 3D, the adhesive 360 can be expelled from the second lumen 210 by inserting the actuator 101 into the second lumen 210 and distally advancing the actuator 101 relative to the housing 202. The actuator 101 can be inserted into the second lumen 210 after advancing the housing 202 into the tissue opening. According to various embodiments, the actuator 101 can be inserted in the second lumen 210 while advancing the housing 202 into the tissue opening. As described in greater detail below with reference to FIGS. 4-10B, an actuator of the present technology can be slidably advanced (e.g., in a distal direction), slidably retracted (e.g., in a proximal direction), and/or rotated relative to the housing to expel the adhesive 360.

The adhesive 360 can move through the apertures 212 into contact with the subcutaneous tissue and/or skin defining the tissue opening. It can be advantageous for the outer wall 206 of the housing 202 to be positioned in contact with the subcutaneous tissue defining the tissue opening so that, when the adhesive 360 is expelled from the housing 202, the adhesive immediately contacts the subcutaneous tissue and is not able to prolapse through the tissue opening and into the vessel opening. The adhesive 360 can be delivered in a thin layer to one or more portions of the subcutaneous tissue. Delivering the adhesive 360 through the sidewall apertures 212, rather than through a distal opening, of the housing 202 facilitates delivery of the adhesive 360 into the tissue opening but not the vessel opening. Moreover, in some embodiments, only a small volume of adhesive 360 is delivered to the tissue opening such that all the adhesive 360 adheres to the subcutaneous tissue and/or skin and is therefore unable to prolapse into the vessel opening. Various embodiments of the present technology are directed to housing and actuator designs that facilitate such delivery of the adhesive 360.

The adhesive 360 can have a viscosity sufficiently high such that the adhesive 360 does not inadvertently prolapse from the tissue opening into the vessel opening. According to various embodiments, a viscosity of the adhesive 360 can be between about between about 5,000 centipoise (cP) and about 25,000 cP, for example between about 10,000 cP and about 20,000 cP. The adhesive 360 can have a viscosity of at least 5,000 cP, at least 10,000 cP, at least 15,000 cP, at least 20,000 cP, at least 25,000 cP, or at least 30,000 cP. In some embodiments, the adhesive 360 can have a lower viscosity to facilitate passage of the adhesive 360 through the apertures 212 of the housing 202. For example, the adhesive 360 can have a viscosity between about 40 cP and about 5,000 cP.

Figure 3E:
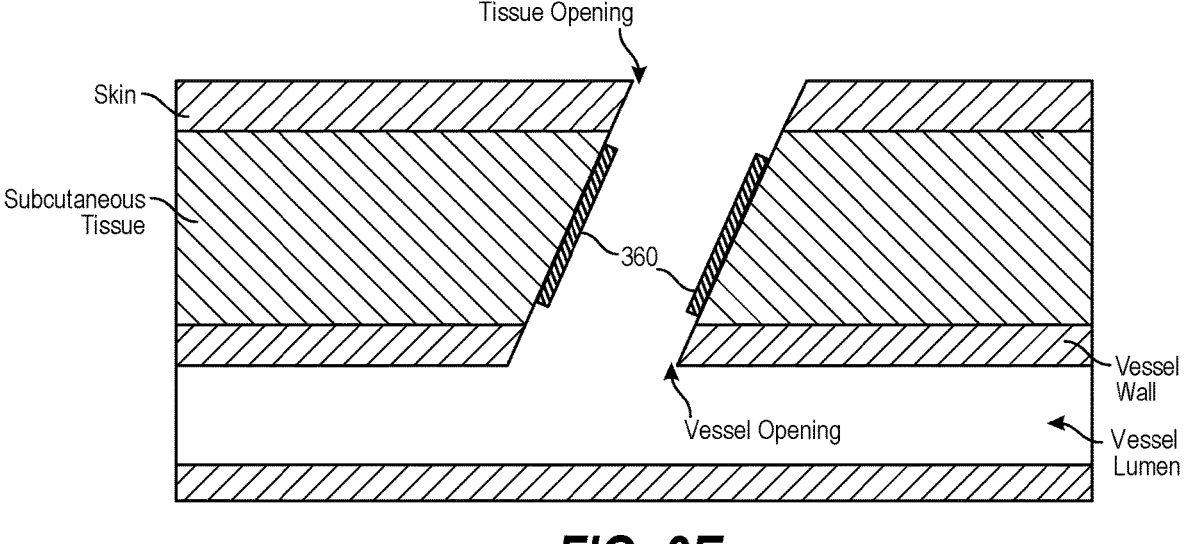
Figure 3F:
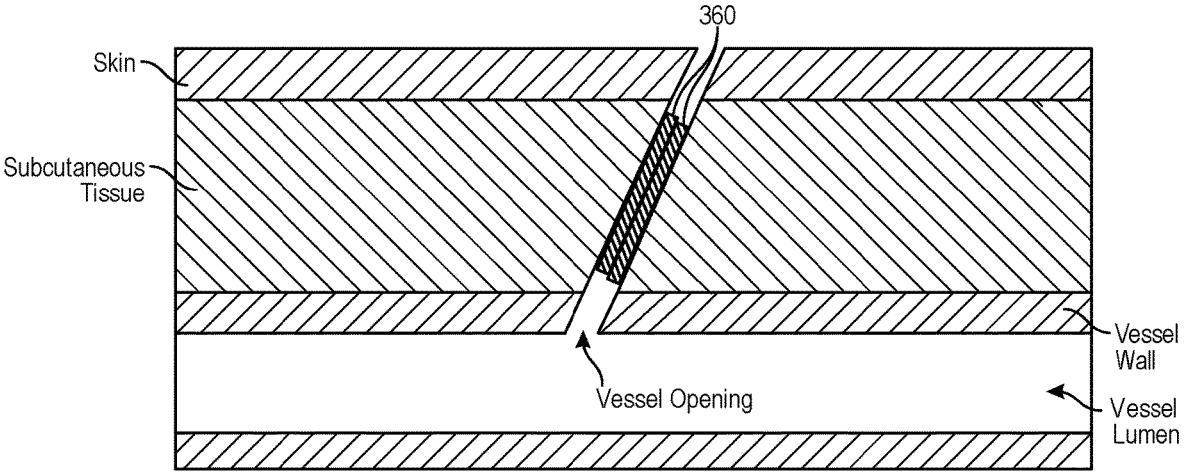

Once the adhesive 360 has been delivered to the tissue opening, the housing 202, the actuator 101, and/or the elongate member 350 can be removed from the tissue opening (see FIG. 3E). Upon removal of the housing 202 from the tissue opening, opposing portions of the subcutaneous tissue defining the tissue opening can collapse onto one another (see FIG. 3F). Additionally or alternatively, an operator can apply traction and/or pressure to the skin to bring the opposing portions of the subcutaneous tissue together. When the tissue opening is angled, as shown in FIGS. 3A-3F, even perpendicular pressure applied to the skin can cause the opposing portions of the subcutaneous tissue to collapse upon one another without forcing the adhesive 360 into the vessel opening. The adhesive 360 can cause the opposing portions of the subcutaneous tissue to adhere together, thereby closing the tissue opening and preventing blood from flowing through the vessel opening. Additionally or alternatively, the adhesive 360 itself can block the vessel opening to prevent or limit blood flow out of the vessel opening. The vessel opening can heal through biological mechanisms while the subcutaneous tissue and/or adhesive prevent blood flow through the vessel opening.

The adhesive 360 can be configured to polymerize, cure, dry, harden, and/or otherwise set once delivered to the tissue opening. In some examples, the adhesive 360 can have a setting time of between about 5 seconds to about 120 seconds, about 10 seconds to about 90 seconds, about 30 seconds to about 60 seconds, about 10 seconds, about 30 seconds, about 60 seconds, about 90 seconds, or about 120 seconds. The adhesive 360 can be configured to set in response to exposure to an activator such as light (e.g., ultraviolet, infrared, etc.), air, blood, tissue, other chemicals, mechanical force, etc. The exposure can occur upon expelling the adhesive 360 from the housing 202 into the tissue opening and/or the exposure can be provided by an operator. In some embodiments, the setting time of the adhesive 360 can be sufficiently long to facilitate the opposing portions of the subcutaneous tissue being brought into contact with one another (e.g., via collapse of the tissue opening on its own, traction and/or pressure applied by the operator, etc.) prior to setting of the adhesive 360.

FIGS. 4-10B illustrate representative examples of adhesive delivery devices 400, 600, 800, 1000 in accordance with various embodiments of the present technology. The features of the adhesive delivery devices 400, 600, 800, 1000 can be generally similar to the features of the adhesive delivery device 100 of FIG. 1. Accordingly, like numbers (e.g., second lumen 410 versus second lumen 210) are used to identify similar or identical components in FIGS. 1-10B, and the discussion of the adhesive delivery devices 400, 600, 800, 1000 of FIGS. 4-10B will be largely limited to those features that differ from the adhesive delivery device 100. Additionally, any of the features of the adhesive delivery devices 400, 600, 800, 1000 of FIGS. 4-10B can be combined with each other and/or with the features of the adhesive delivery device 100. Any of the systems and methods disclosed herein can include or use, respectively, any of the adhesive delivery devices 100, 400, 600, 800, 1000.

As previously noted, an adhesive delivery device of the present technology can utilize movement of the actuator relative to the housing to expel adhesive from the housing into a tissue opening. FIGS. 4-10B illustrate example adhesive delivery devices 400, 600, 800, 1000 utilizing various types of actuator movement (e.g., longitudinal sliding, rotation, etc.) to deliver an adhesive. As discussed in greater detail herein, the different types of actuator movement and/or the unique designs of the adhesive delivery devices 400, 600, 800, 1000 can provide certain advantages, such as delivering a small, controlled volume of adhesive, preventing the adhesive from being delivered into the vessel opening, preventing inadvertent delivery of the adhesive, and others.

Figure 5:
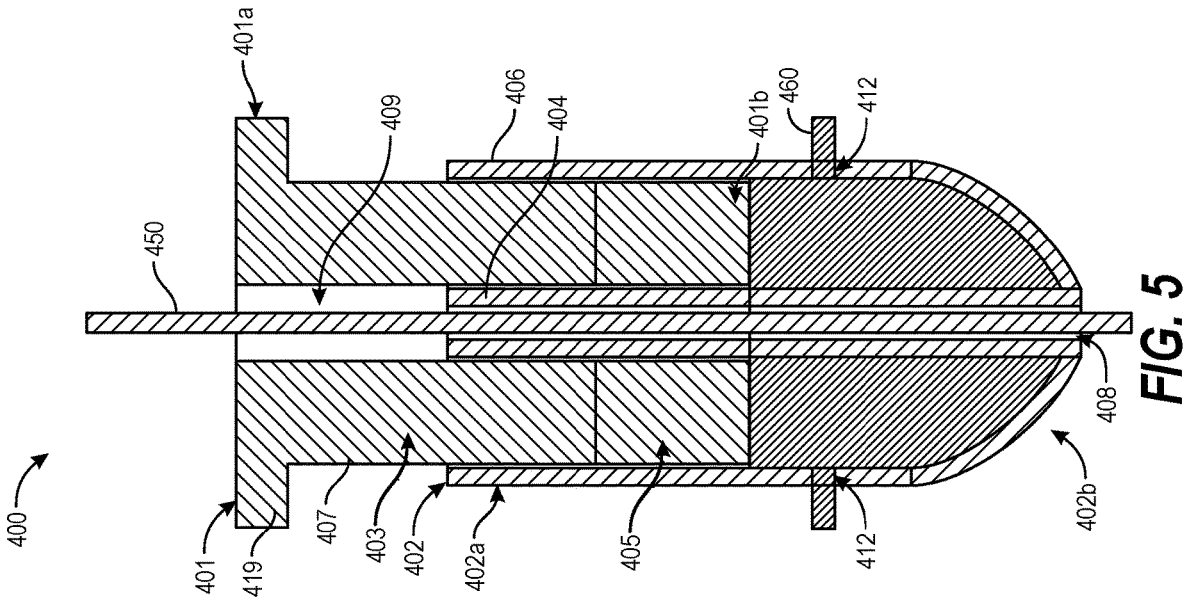
FIGS. 4 and 5 are cross-sectional views of an adhesive delivery device in a pre-delivery configuration and a delivery configuration, respectively, in accordance with several embodiments of the present technology.
Figure 4:
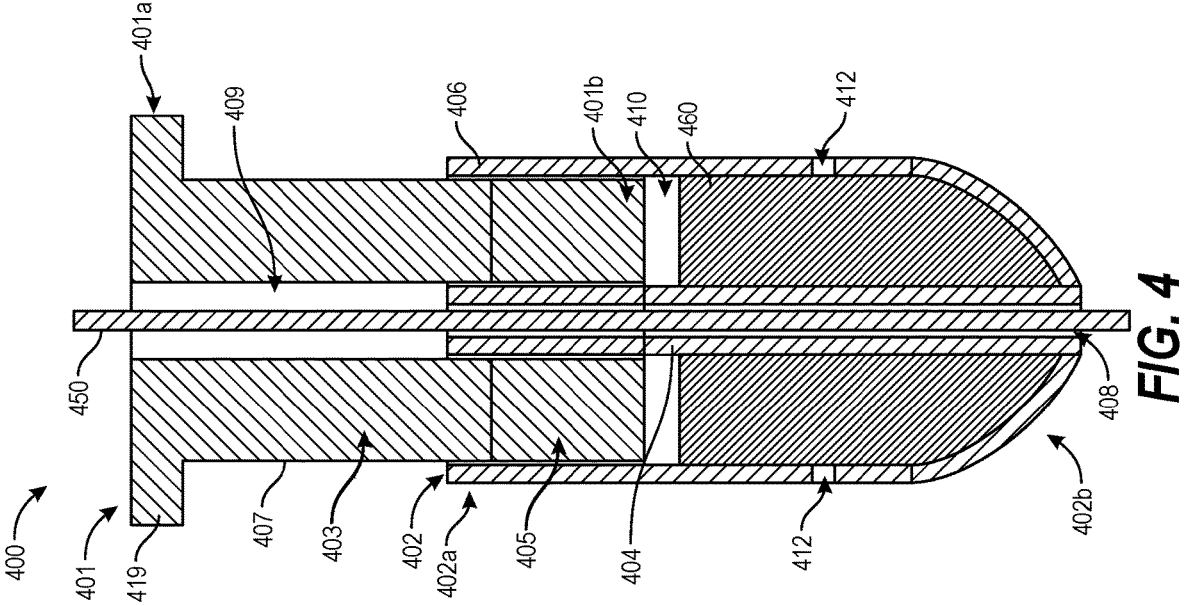

FIGS. 4 and 5 are cross-sectional views of an adhesive delivery device 400 (also "device 400") comprising an actuator 401 and a housing 402 in accordance with various embodiments of the present technology. FIG. 4 illustrates the device 400 in a pre-delivery configuration with an adhesive 460 retained within the housing 402 and FIG. 5 illustrates the device 400 in a delivery configuration with the adhesive 460 being expelled from the housing 402 by the actuator 401. As illustrated in FIGS. 4 and 5, in some embodiments, the actuator 401 can be configured to be distally advanced relative to the housing 402 to expel the adhesive 460.

In some embodiments, the second lumen 410 of the housing 402 is circumferentially continuous and completely circumferentially surrounds the first lumen 408. The second lumen 410 can be configured to receive and retain the adhesive 460. In the pre-delivery configuration (see FIG. 4), the adhesive 460 can be substantially longitudinally aligned with the apertures 412. It may be advantageous for the adhesive 460 to have a sufficiently high viscosity to prevent or limit inadvertent flow of the adhesive 460 from the second lumen 410 out of the apertures 412 in embodiments in which the adhesive 460 is aligned with the apertures 412 in the pre-delivery and/or as-packaged configuration. In some embodiments, a sufficient volume of the adhesive 460 can be positioned within the second lumen 410 such that the adhesive 460 substantially fills the second lumen 410 from a distal end of the second lumen 410 to a location at or proximal of the apertures 412 of the housing 402. Although not shown in FIGS. 4 and 5, in some embodiments, the housing 402 can include an internal wall extending radially across the second lumen 410 that prevents the adhesive 460 from reaching the distal end of the second lumen 410. In such embodiments, the apertures 412 can be located at a desired longitudinal distance from the distal end of the housing 402 while limiting the volume of adhesive 460 required to be positioned within the second lumen 410 to have the adhesive 460 longitudinally aligned with the apertures 412.

As shown in FIGS. 4 and 5, an inner wall 404 of the housing 402 defines a first lumen 408 configured to receive an elongate member 450. The elongate member 450 can be coaxial and/or concentric with the inner wall 404 when positioned within the first lumen 408. As previously noted, the first lumen 408 can have a diameter at least as large as an outer diameter of the elongate member 450 such that the housing 402 can be slidably advanced over the elongate member 450. The actuator 401 can be aligned with the housing 402 prior to inserting the actuator 401 into the second lumen 410 of the housing 402 by positioning the elongate member 450 within the channel 409 of the actuator 401. The elongate member 450 can be coaxial and/or concentric with the sidewall 407 of the actuator 401 when positioned within the channel 409.

The plunger 405 and at least a portion of the shaft 403 can be configured to be inserted into and distally advanced within the second lumen 410, for example to expel the adhesive 460 from the second lumen 410. The inner wall 404 of the housing 402 can be positioned within the channel 409 when inserting the plunger 405 and/or shaft 403 into the second lumen 410. In some embodiments, the inner wall 404 is coaxial and/or concentric with the sidewall 407 of the actuator 401 when positioned within the channel 409. In some embodiments, an outer diameter of the plunger 405 and/or shaft 403 substantially corresponds to and/or is at least as large as the outer diameter of the second lumen 410 such that the plunger 405 and/or shaft 403 substantially radially fill the second lumen 410. Although not shown in FIGS. 4 and 5, in some embodiments the plunger 405 can have an outer diameter at least as large as the outer diameter of the second lumen 410 while the shaft 403 has an outer diameter smaller than the outer diameter of the second lumen 410. The smaller outer diameter of the shaft 403 can facilitate sliding the actuator 401 through the second lumen 410 without developing significant friction while the larger outer diameter of the plunger 405 can prevent leakage of the adhesive 460 past the plunger 405. It may be advantageous for the plunger 405 to have an outer diameter larger at least as large as the outer diameter of the second lumen 410 along only a limited portion of its length to facilitate sliding of the actuator 401 through the second lumen 410 without developing significant friction.

With at least the plunger 405 positioned in the second lumen 410, distal advancement of the actuator 401 increases pressure within the second lumen 410, forcing the adhesive 460 to move from an area of high pressure (within the second lumen 410) to an area of lower pressure (an environment external to the housing 402) via the apertures 412. As shown in FIG. 5, a distal end of the plunger 405 can contact the adhesive 460 as the actuator 401 is distally advanced through the second lumen 410. Distal advancement of the actuator 401 to expel the adhesive 460 can provide a simple mechanism for delivering adhesive to a tissue opening. Additionally, the device 400 facilitates loading of the adhesive 460 into the second lumen 410 and insertion of the actuator 401 into the second lumen 410 at a variety of timepoints (e.g., before advancing the housing 402 into the tissue opening, after advancing the housing 402 into the tissue opening, etc.), providing for a flexible method of treating a vessel opening with the device 400.

The actuator 401 can be distally advanced through the second lumen 410 until a desired amount of adhesive 460 has been expelled from the second lumen 410. In some embodiments, the device 400 includes a mechanical stop configured to prevent further distal advancement of the actuator 401 once the desired amount of adhesive 460 has been expelled. For example, as shown in FIGS. 4 and 5, the distal end of the plunger 405 can be blunt (e.g., not tapered) while the distal end of the outer wall 406 of the housing 402 is tapered. In such embodiments, and others, the distal end of the plunger 405 can engage the outer wall 406 of the housing 402 once the actuator 401 has been distally advanced through the second lumen 410 by a predetermined amount. Alternatively, the distal end portion 401*b* of the actuator 401 can be tapered to mirror the tapering of the outer wall 406 of the housing 402. As shown in FIGS. 4 and 5, the actuator 401 can include a projection 419 at the proximal end portion 401*a* of the actuator 401. The projection 419 can have an outer diameter greater than an outer diameter of the intermediate portion 401*c* and/or the distal end portion 401*b* of the actuator 401. The projection 419 of the actuator 401 can be configured to engage the outer wall 406 of the housing 402 once the actuator 401 has been distally advanced through the second lumen 410 by a predetermined amount. Alternatively, the outer diameter of the sidewall 407 can be substantially the same at the proximal end portion 401*a* of the actuator 401 and at the shaft 403. Although not shown in FIGS. 4 and 5, in some embodiments, the proximal end portion 402*a* of the housing 402 includes a projection having an outer diameter greater than an outer diameter of the intermediate portion 402*c* and/or the distal end portion 402*b* of the housing 402. The projection of the housing 402 can be configured to contact the projection 419 of the actuator 401 once the actuator 401 has been advanced through the second lumen 410 by a predetermined distance. In some embodiments, the actuator

401 and/or the housing 402 include one or more visual markers configured to identify when the actuator 401 has been sufficiently distally advanced within the second lumen 410.

Figures 6A, 6B, 6C:
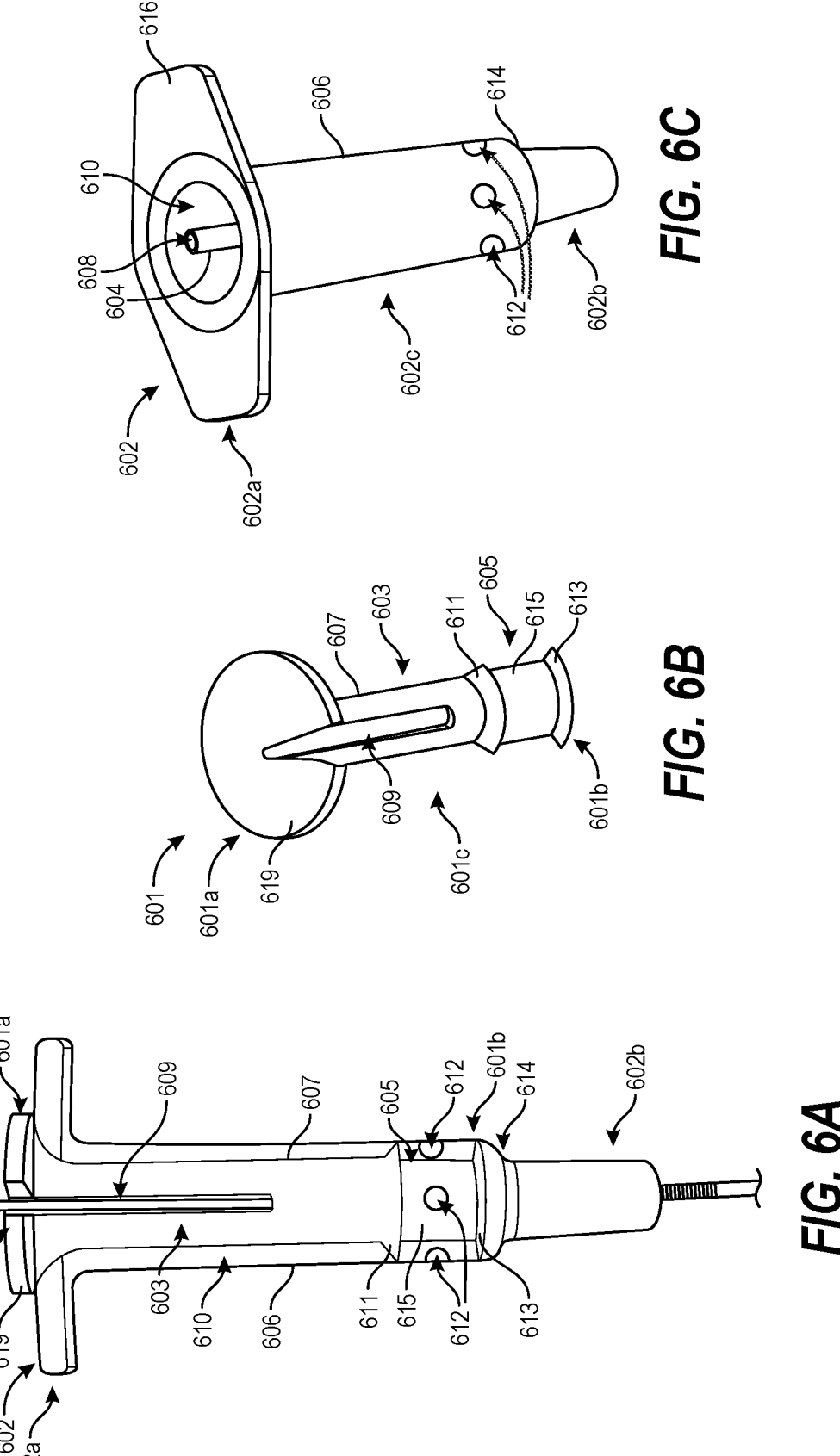
FIG. 6A illustrates an adhesive delivery device in accordance with several embodiments of the present technology.
FIG. 6B is an isolated view of an actuator of the adhesive delivery device of FIG. 6A
FIG. 6C is an isolated view of a housing of the adhesive delivery device of FIG. 6A.

FIGS. 6A-7B illustrate another example adhesive delivery device 600 (also "device 600") in accordance with several embodiments of the present technology. Similar to the devices previously disclosed herein, the device 600 comprises an actuator 601 (shown isolated in FIG. 6B) and a housing (shown isolated in FIG. 6C). FIG. 6A illustrates the housing as having a transparent outer wall for case of visualization, whereas FIG. 6C illustrates the housing as having an opaque outer wall. FIG. 6A illustrates the device 600 in a pre-delivery configuration in which the actuator 601 is received within the housing 602. The pre-delivery configuration can comprise a configuration of the device 600 while advancing the device 600 into the tissue opening and/or prior to adhesive being expelled from the housing 602. Whereas the previously disclosed housing 402 of FIGS. 4 and 5 retains adhesive in a distal portion of the second lumen such that the adhesive is positioned distal of the actuator and distal advancement of the actuator causes the adhesive to be expelled from the housing, the actuator 601 of FIGS. 6A-6C defines a chamber region within which the adhesive can be positioned in the pre-delivery configuration. Proximal retraction and/or distal advancement of the actuator 601 can cause adhesive to be expelled from the housing 602.

Like the previously disclosed actuators 101, 401 the actuator 601 can comprise a shaft 603 and a plunger 605. Similar to shafts 103, 403, the shaft 603 can have an outer diameter that is substantially constant along its length. However, where the plungers 105, 405 are shown as having a substantially constant outer diameter along their lengths, as shown in FIGS. 6A and 6B, an outer diameter of the plunger 605 can vary along its length. Specifically, the plunger 605 can include a proximal flange 611, a distal flange 613 opposite the proximal flange 611 along a longitudinal dimension of the plunger 605, and an intermediate wall 615 therebetween. The proximal flange 611 and the distal flange 613 can each have an outer diameter larger than outer diameter of the intermediate wall 615 such that the proximal and distal flanges 611, 613 and the intermediate wall 615 define a chamber region. As discussed in greater detail with reference to FIGS. 7A and 7B, the chamber region can be configured to receive an adhesive.

An outer diameter of the proximal flange 611 and/or the distal flange 613 can substantially correspond to and/or be at least as large as an outer diameter of the second lumen 610 of the housing 602 such that, when the plunger 605 is inserted within the second lumen 610, the proximal and distal flanges 611, 613 are in contact with the outer wall 606 of the housing 602. Thus, the chamber region can be sealed longitudinally between the proximal and distal flanges 611, 613 and radially between the intermediate wall 615 and the outer wall 606 of the housing 602. The proximal flange 611 and/or the distal flange 613 can comprise a flexible material such that an outer rim of the flange remains engaged with the outer wall 606 of the housing 602 but the flange is able to deform as the actuator 601 longitudinally slides within the second lumen 610. In some embodiments, the proximal flange 611 and/or the distal flange 613 can be sufficiently rigid to overcome friction between outer wall 606 and the flange when the actuator 601 is sliding within the second lumen 610.

In some embodiments, for example as shown in FIGS. 6A and 6B, the sidewall 607 of the actuator 601 can be split (e.g., circumferentially discontinuous) along at least a portion of its length such that the channel 609 defined by the sidewall 607 is open along at least a portion of its length (e.g., the sidewall 607 only partially circumferentially surrounds the channel 609). In embodiments in which the sidewall 607 is not split and the channel 609 is completely circumferentially enclosed by the sidewall 607, an elongate member 650 can be inserted into the channel 609 and manipulated only at the proximal and distal end portions of the channel 609. However, when the channel 609 is open along at least a portion of its length, the elongate member 650 can be inserted into and/or removed from the channel 609 along an intermediate portion of the channel 609. Thus, a split actuator sidewall 607 can facilitate insertion, removal, and/or manipulation of the elongate member 650 within the channel 609.

The actuator 601 can include a projection 619 at the proximal end portion 601a of the actuator 601 that has a diameter greater than a diameter of the actuator 601 along the distal end portion 601b and/or the intermediate portion 601c. The projection 619 can be monolithic with the shaft 603 or separately formed and later coupled to the shaft 603. As shown in FIG. 6B, the channel 609 can extend along the intermediate portion 601c and into the projection 619 such that the channel 609 terminates proximally within or at the proximal surface of the projection 619.

As shown in FIGS. 6A and 6C, in some embodiments an outer diameter of the housing 602 can be greater at the proximal end portion 602a of the housing than at the distal end portion 602b and/or the intermediate portion 602c. For example, the proximal end portion 602a of the housing 602 can include a projection 616 that is wider than the rest of the housing 602. The projection 616 can be configured to abut the projection 619 of the actuator 601 to provide a mechanical stop limiting distal advancement of the actuator 601 within the second lumen 610. As discussed with reference to housing 202, the outer wall 606 of the housing 602 can taper in a distal direction such that an outer diameter of the outer wall 606 is smallest at the distal end portion 602b of the housing 602. In some embodiments, for example as shown in FIGS. 6A and 6B, the outer diameter of the outer wall 606 of the housing 602 can substantially decrease at a step 614. Distal of the step 614, the outer diameter of the outer wall 606 of the housing 602 can be substantially constant along its length or can taper in a distal direction. In some embodiments, the outer diameter of the outer wall 606 of the housing 602 is substantially constant between the projection 616 and the step 614. In some embodiments, in place of the step 614, the outer diameter of the outer wall 606 of the housing 602 can taper smoothly along a larger length of the housing 602. Still, in some embodiments the outer wall 606 of the housing 602 is not tapered.

Figure 7A:
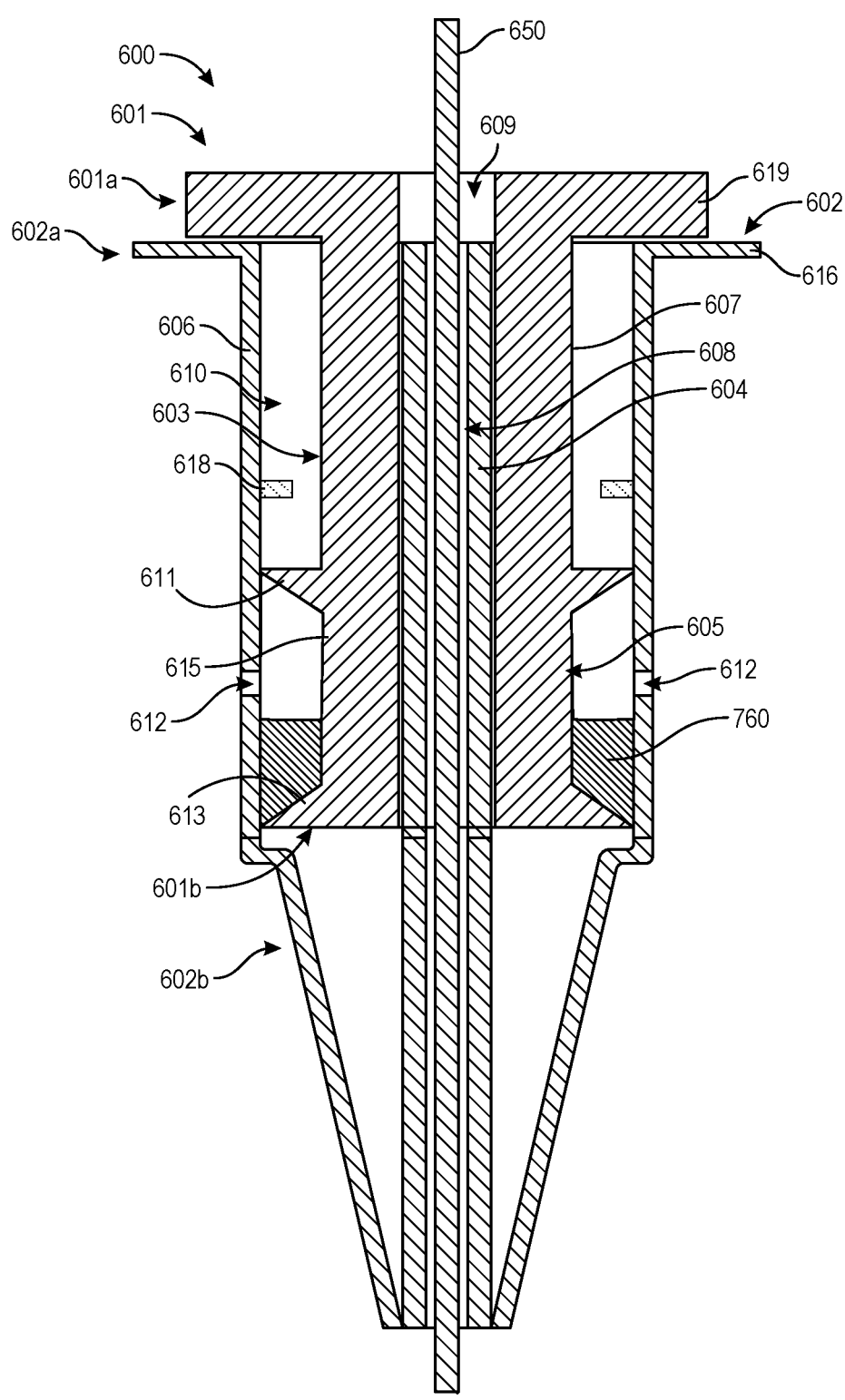
FIGS. 7A and 7B are cross-sectional views of the delivery device of FIGS. 6A-6C in a pre-delivery configuration and a delivery configuration, respectively, in accordance with several embodiments of the present technology.
Figure 7B:
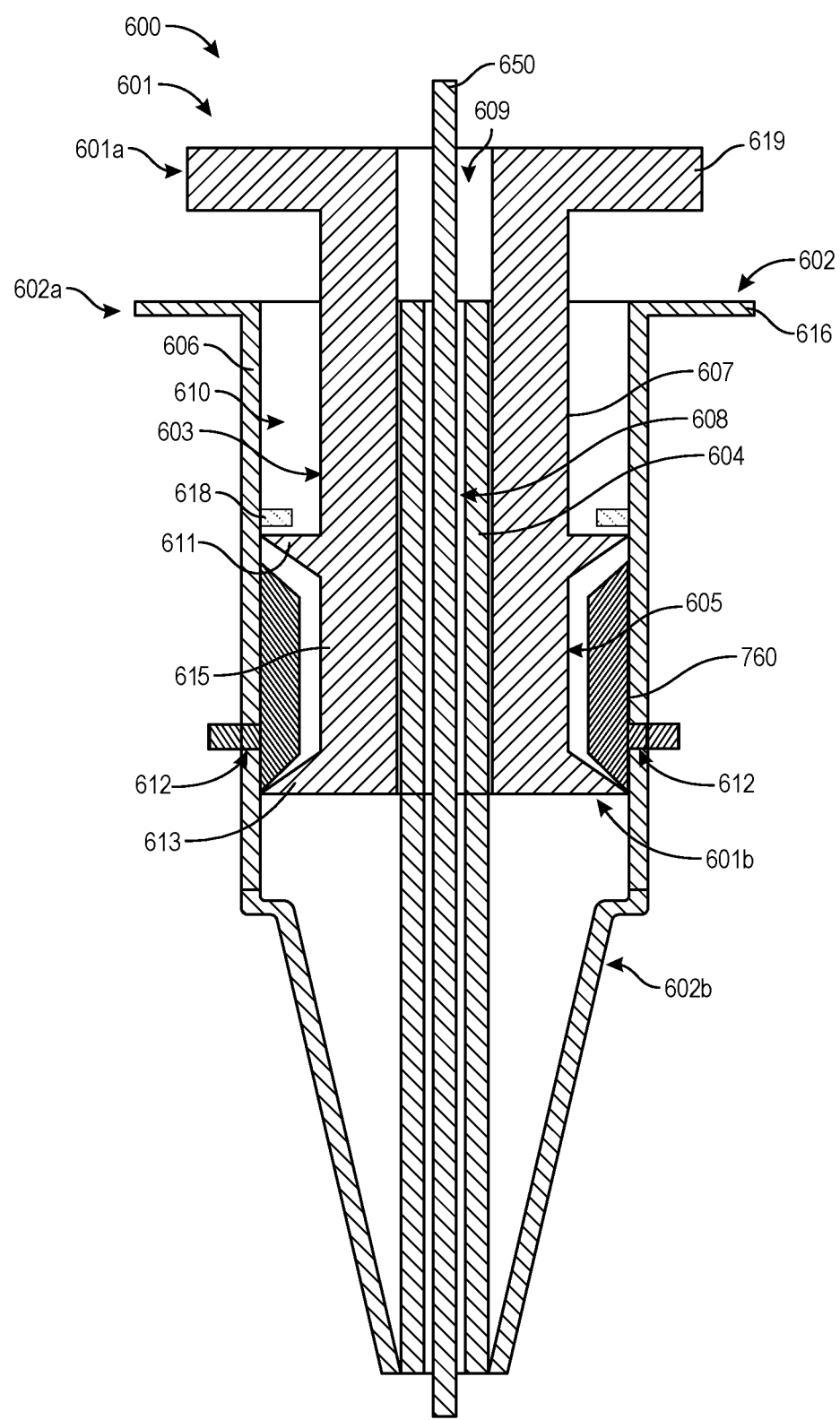

FIGS. 7A and 7B are cross-sectional views of the device 600 of FIGS. 6A-6C with the device 600 in a pre-delivery configuration and a delivery configuration, respectively. In at least the pre-delivery configuration, the plunger 605 can be positioned within the second lumen 610 of the housing 602 with the inner wall 604 of the housing 602 positioned within the channel 609 of the actuator 601. An adhesive 760 can be positioned within the chamber region that is defined longitudinally between the proximal and distal flanges 611, 613 of the plunger 605 and radially between the intermediate wall 615 of the plunger 605 and the outer wall 606 of the housing 602. The adhesive 760 may or may not substantially fill the chamber region. For example, as shown in FIG. 7A, in some embodiments the adhesive 760 does not substantially fill the chamber region and is positioned at a distal portion of the chamber region. Additionally or alternatively, the adhesive 760 can be positioned along any longitudinal or circumferential position within the chamber region. In any case, longitudinal movement of the actuator 601 from the pre-delivery configuration to the delivery configuration can force the adhesive 760 to move through the apertures 612 and be expelled from the second lumen 610.

In some embodiments, for example as shown in FIGS. 7A and 7B, proximal retraction of the actuator 601 from the pre-delivery configuration to the delivery configuration can force the adhesive 760 to move through the apertures 612. According to some examples, the apertures 612 can be positioned longitudinally between the proximal and distal flanges 611, 613 of the plunger 605 when the device 600 is in the pre-delivery configuration. Proximal retraction of the actuator 601 can cause the distal flange 613 to move proximally, thereby moving the adhesive 760 within the chamber region proximally as well. In embodiments in which the adhesive 760 is disposed distally of the apertures 612, proximal retraction of the actuator 601 can cause a thin layer of the adhesive 760 to be dispensed along an inner surface of the outer wall 606 at the apertures 612 and move through the apertures 612 as the distal flange 613 moves proximally. In other words, proximal retraction of the actuator 601 can cause the adhesive 760 to longitudinally align with the apertures 612. Additionally or alternatively, proximal retraction of the actuator 601 can cause the adhesive 760 to move radially outwardly within the chamber region towards the outer wall 606 and apertures 612. In some embodiments, the pressure within the chamber region can increase as the actuator 601 is proximally retracted to facilitate movement of the adhesive 760 through the apertures 612. Advantageously, delivering the adhesive 760 by proximally retracting the actuator 601 can prevent or limit the adhesive 760 from being pushed distally towards and/or into the vessel opening. Moreover, delivering the adhesive 760 by spreading a thin layer of adhesive 760 over the outer wall 606 of the housing 602 and the apertures 612 enables a small, controlled volume of adhesive 760 to be delivered to the tissue opening, which can prevent or limit prolapse of the adhesive 760 from the tissue opening into the vessel opening.

The proximal flange 611 can prevent the adhesive 760 from inadvertently exiting the second lumen 610 through the proximal end portion 602a of the housing 602. However, the proximal flange 611 may not be necessary for expelling the adhesive 760 by proximally retracting the actuator 601. Thus, in some embodiments, the plunger 605 may omit the proximal flange 611.

In the example shown in FIGS. 7A and 7B, the apertures 612 are positioned longitudinally between the proximal and distal flanges 611, 613 of the plunger 605 when the device 600 is in the pre-delivery configuration. The adhesive 760 positioned between the proximal and distal flanges 611, 613 may therefore be longitudinally aligned with the apertures 612 in the pre-delivery configuration. In some embodiments, it may be advantageous to prevent the adhesive 760 from being aligned with apertures 612 in the pre-delivery configuration, to prevent or limit inadvertent expulsion of the adhesive 760 from the second lumen 610. Thus, in some embodiments, the proximal flange 611 of the plunger 605 can be located distally of the apertures 612 when the device 600 is in the pre-delivery configuration. As the actuator 601 is proximally retracted, the proximal flange 611 can move proximally past the apertures 612 such that the chamber region and the adhesive 760 are longitudinally aligned with the apertures 612 and the adhesive 760 can move through the apertures 612.

Although the device 600 shown in FIGS. 6A-7B has been described as utilizing proximal retraction of the actuator 601 to expel the adhesive 760, in some embodiments the actuator 601 can be advanced distally relative to the housing 602 to expel the adhesive 760. Such embodiments may still be advantageously configured to deliver a small, controlled volume of adhesive 760 by spreading a thin layer of adhesive 760 over the apertures 612. The distal flange 613 can be positioned proximally of the apertures 612 when the device 600 is in the pre-delivery configuration. To move the device 600 from the pre-delivery configuration to the delivery configuration, the actuator 601 can be advanced distally so that the distal flange 613 moves distally beyond the apertures 612, the chamber region is longitudinally aligned with the apertures 612, and the proximal flange 611 pushes the adhesive 760 into contact with the outer wall 606 of the housing 602 at the apertures 612. Additionally or alternatively, when the device 600 is in the pre-delivery configuration the chamber region and/or the adhesive 760 can be longitudinally aligned with the apertures 612 and distal advancement of the actuator 601 can cause the adhesive 760 to be forced into the apertures 612.

In some embodiments, a distance between the proximal flange 611 and the distal flange 613 is fixed such that the chamber region has a fixed longitudinal dimension. However, in some embodiments, the distal flange 613 can be moveable relative to the proximal flange 611 so that the longitudinal dimension (and thus volume) of the chamber region can be reduced to further facilitate expulsion of the adhesive 760 from the second lumen 610. Reducing the longitudinal dimension of the chamber region can cause pressure to increase within the chamber region, which facilitate movement of the adhesive 760 from the second lumen 610 through the apertures 612.

To enable movement of the proximal and distal flanges 611, 613 relative to one another, the proximal and distal flanges 611, 613 can be carried by separate shafts (not shown). For example, the actuator 601 can comprise a first shaft carrying the proximal flange 611 and a second shaft carrying the distal flange 613. The first and second shafts can be slidable relative to one another so that longitudinal movement of the first and second shafts relative to one another changes the distance between the proximal and distal flanges 611, 613, thereby changing the longitudinal dimension of the chamber region. In some embodiments, the intermediate wall 615 of the actuator 601 can be compressible to enable the distance between the proximal and distal flanges 611, 613 to be reduced.

The housing 602 can include a stop 618 (only shown in FIGS. 7A and 7B) that is configured to limit movement of the proximal flange 611 or the distal flange 613. The stop 618 can be positioned within the second lumen 610. For example, the stop 618 can extend from the outer wall 606 radially inwardly into the second lumen 610 (as shown) and/or from the inner wall 604 radially outwardly into the second lumen 610. The stop 618 can be monolithic with the inner wall 604 and/or the outer wall 606. In some embodiments, the stop 618 comprises a distinct component from the housing 202 that is configured to be positioned and secured within the second lumen 610. The stop 618 can comprise a ring, a protrusion, a bump, a flange, or any other suitable structure for engaging the proximal flange 611 and/or the distal flange 613. In some embodiments, the housing 602 does not include the stop 618.

In embodiments in which proximal retraction of the actuator 601 expels the adhesive 760, the stop 618 can be positioned proximal of the proximal flange 611 of the actuator 601, for example as shown in FIGS. 7A and 7B. The actuator 601 can be free to slide proximally through the second lumen 610 until the proximal flange 611 abuts the stop 618. The proximal flange 611 may stop moving proximally once it contacts the stop 618. However, if movement of the distal flange 613 is decoupled from movement of the proximal flange 611 (e.g., by being carried by a separate shaft, by compression of the intermediate wall 615, etc.), the distal flange 613 can continue moving proximally, thereby reducing the longitudinal dimension of the chamber region and increasing a pressure within the chamber region to expel the adhesive 760 through the apertures 612. Likewise, in embodiments in which distal advancement of the actuator 601 expels the adhesive 760, the stop 618 can be positioned distal of the distal flange 613 of the actuator 601. Further distal advancement of the actuator 601 after the distal flange 613 has engaged the stop 618 can cause the proximal flange 611 to continue advancing while the distal flange 613 remains stationary, reducing the longitudinal dimension of the chamber region.

Figure 8A:
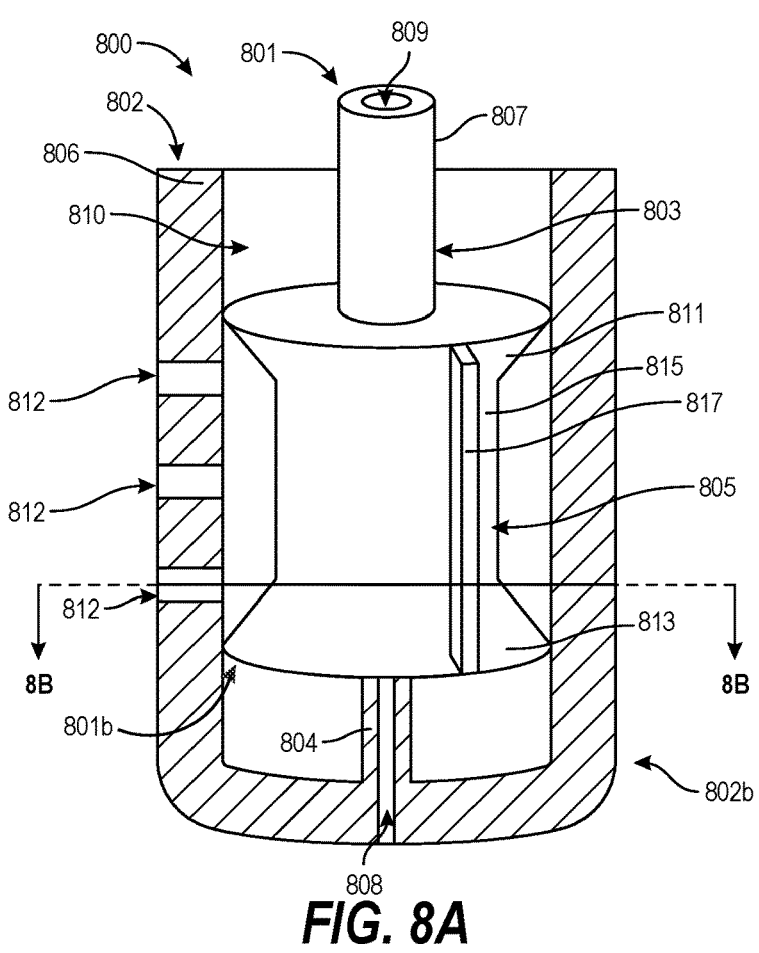
FIG. 8A is a cutaway view of an adhesive delivery device in a pre-delivery configuration in accordance with several embodiments of the present technology.
Figure 8B:
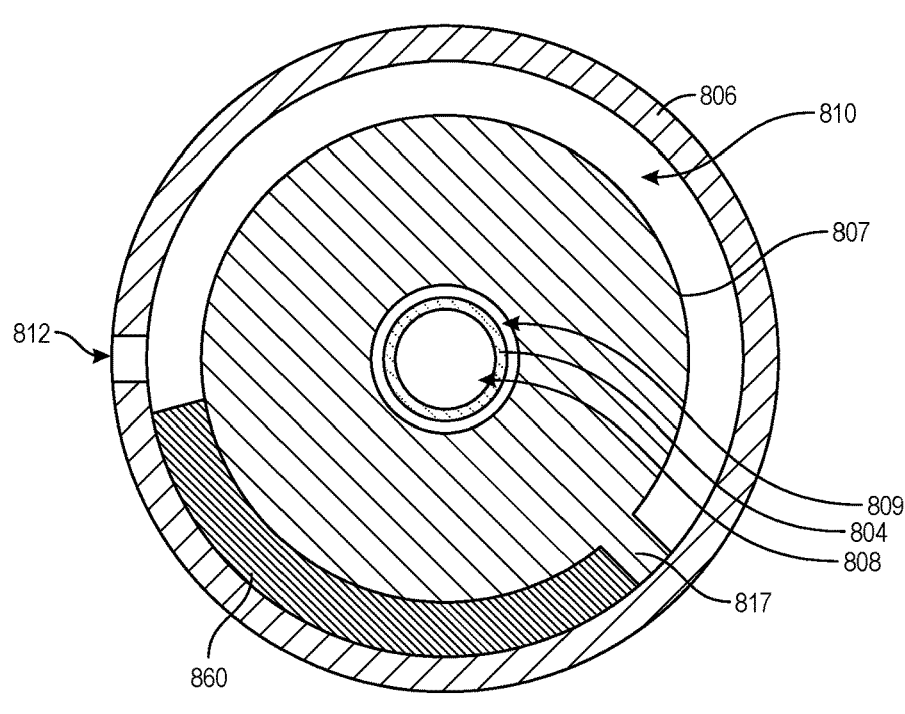
FIG. 8B is an axial cross-sectional view of the adhesive delivery device of FIG. 8A.
Figure 9A:
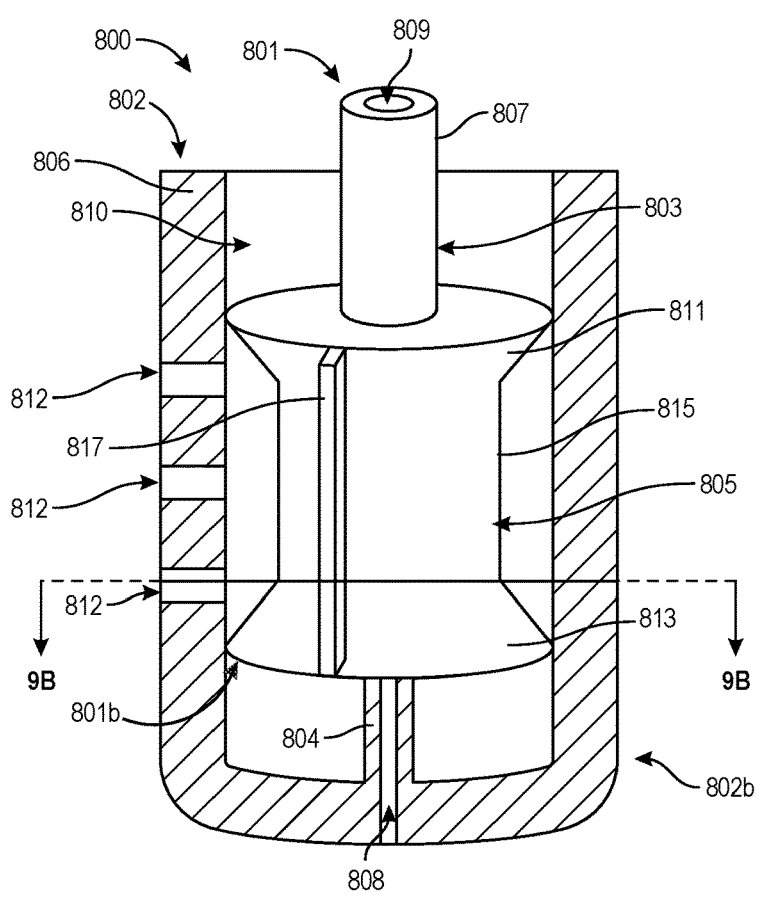
FIGS. 9A and 9B are cutaway and axial cross-sectional views of the adhesive delivery device of FIGS. 8A and 8B in a delivery configuration.
Figure 9B:
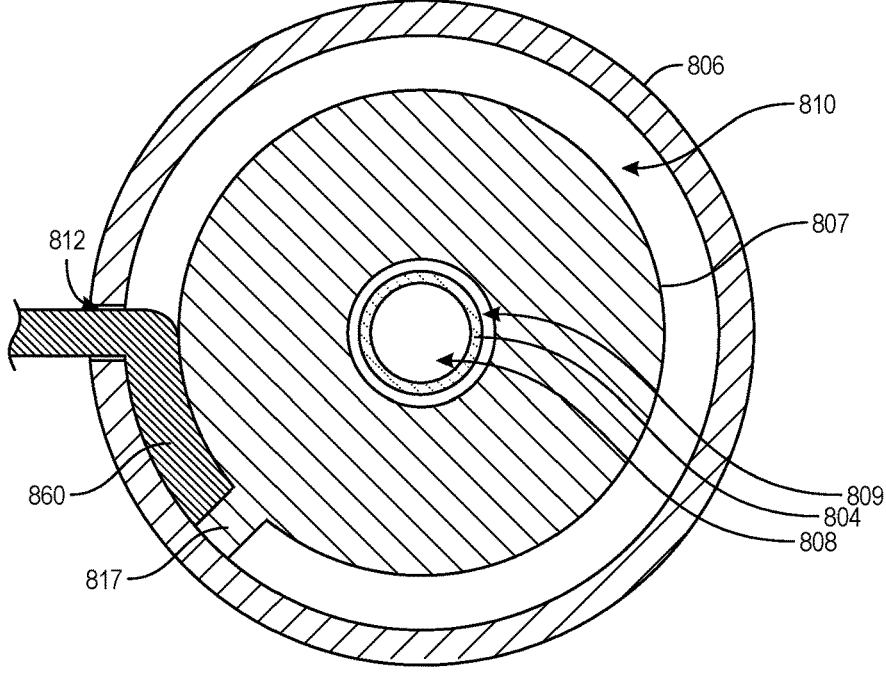

The adhesive delivery devices disclosed herein thus far utilize longitudinal sliding of the actuator relative to the housing to expel the adhesive from the apertures. However, in some embodiments, the actuator can be rotated relative to the housing to expel the adhesive from the apertures. FIGS. 8A-9B illustrate an example of such a device 800. FIGS. 8A and 8B are cutaway and axial cross-sectional views, respectively, of the device 800 in a pre-delivery configuration and FIGS. 9A and 9B are cutaway and axial cross-sectional views, respectively, of the device 800 in a delivery configuration. Only FIGS. 8B and 9B depict the adhesive 860 for ease of visualizing the actuator 801 in FIGS. 8A and 9A.

Similar to the previously disclosed devices, the device 800 comprises a housing 802 configured to receive and retain an adhesive 860 and an actuator 801 configured to force the adhesive 860 to be expelled from the housing 802. As shown in FIG. 8A, the plunger 805 of the actuator 801 can comprise a proximal flange 811, a distal flange 813, and an intermediate wall 815 between the proximal and distal flanges 811, 813. The plunger 805 can define a chamber region between the proximal and distal flanges 811, 813, and the adhesive 860 can be positioned in the chamber region longitudinally between the proximal and distal flanges 811, 813. The plunger 805 also includes a rib 817. The rib 817 can extend radially away from the sidewall 807 of the actuator 801 such that, when the plunger 805 is positioned within the second lumen 810 of the housing 802, the rib 817 extends radially across the second lumen 810 to the outer wall 806 of the housing 802 (see FIG. 8B). The rib 817 can engage the outer wall 806 of the housing 802 to prevent leakage of adhesive past the rib 817. The rib 817 can extend longitudinally along at least a portion of the length of the plunger 805. For example, the rib 817 can extend along the entire length of the intermediate wall 815 of the plunger 805. In some embodiments, the rib 817 extends from the proximal flange 811 to the distal flange 813 (e.g., along the entire length of the plunger 805).

As shown in FIG. 8B, when the device 800 is in the pre-delivery configuration, the adhesive 860 can be positioned radially between the sidewall 807 of the actuator 801 at the intermediate wall 815 and the outer wall 806 of the housing 802. The adhesive 860 can be longitudinally aligned with the apertures 812. In some embodiments, for example as shown in FIG. 8A, the housing 802 can comprise multiple apertures 812 that are at least partially circumferentially aligned and at least partially longitudinally offset. Additionally or alternatively, the housing 802 can comprise one or more apertures 812 that are at least partially circumferentially offset and/or one or more apertures 812 that are at least partially longitudinally aligned. The adhesive 860 can be circumferentially aligned with the apertures 812 or can be circumferentially offset from the apertures 812 when the device 800 is in the pre-delivery configuration.

The rib 817 can be configured to move into contact with the adhesive 860 to force the adhesive 860 through the apertures 812 of the housing 802. Specifically, the actuator 801 can be configured to rotate such that the rib 817 engages the adhesive 860 and moves the adhesive 860 circumferentially though the second lumen 810 of the housing 802. In some embodiments, for example as shown in FIG. 8B, the adhesive 860 may be circumferentially spaced apart from the apertures 812 when the device 800 is in the pre-delivery configuration. Rotation of the actuator 801 can cause the rib 817 to push the adhesive 860 circumferentially towards the apertures 812 and/or to spread the adhesive 860 along the outer wall 806 of the housing 802 at the apertures 812 so that the adhesive 860 is forced through the apertures 812 (see FIGS. 9A and 9B). Alternatively, the adhesive 860 can be circumferentially aligned with the apertures 812 when the device 800 is in the pre-delivery configuration. In such embodiments, rotation of the actuator 801 can still cause the adhesive 860 to be forced through the apertures 812. Rotation of the actuator 801 can increase a pressure within the second lumen 810 to facilitate movement of the adhesive 860 through the apertures 812.

Figures 10A, 10B:
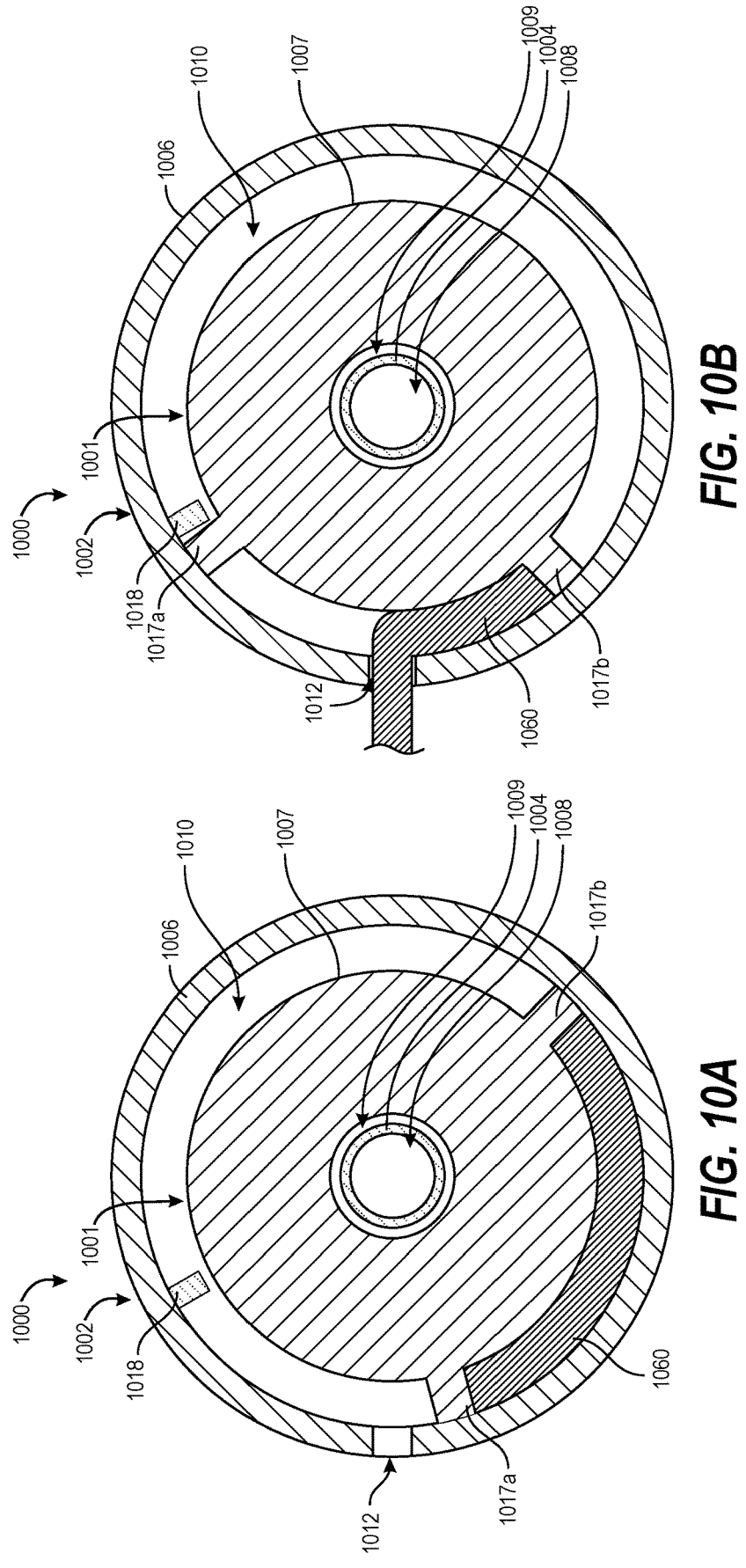
FIGS. 10A and 10B are axial cross-sectional views of an adhesive delivery device in a pre-delivery configuration and a delivery configuration, respectively, in accordance with several embodiments of the present technology.

In some embodiments, it may be advantageous to prevent the adhesive 860 from becoming circumferentially aligned with the apertures 812 in the pre-delivery configuration to prevent the adhesive 860 from being inadvertently expelled from the housing 802. As shown in FIGS. 10A and 10B, in some embodiments, an actuator 1001 can comprise multiple ribs 1017 defining one or more circumferential chamber regions configured to receive the adhesive 1060. A circumferential chamber region containing the adhesive 1060 can be circumferentially offset from the apertures 1012 when the device 1000 is in the pre-delivery configuration to prevent inadvertent delivery of the adhesive 1060. FIGS. 10A and 10B illustrate the actuator 1001 comprising a first rib 1017a and a second rib 1017b, however, the actuator 1001 can include more than two ribs 1017 in some embodiments (e.g., three ribs 1017, four ribs 1017, five ribs 1017, etc.). The adhesive 1060 can be positioned circumferentially between the first and second ribs 1017a, 1017b. Thus, in the pre-delivery configuration, adhesive 1060 can be separated from the apertures 1012 by the ribs 1017. The actuator 1001 can be rotated from the pre-delivery configuration to the delivery configuration (see FIG. 10B) so that the first rib 1017a moves circumferentially past the apertures 1012 and the circumferential chamber region and adhesive 1060 are circumferentially aligned with the apertures 1012. The second rib 1017b can engage the adhesive 1060 and push the adhesive 1060 through the second lumen 1010 and/or can spread the adhesive 1060 in a thin layer along the outer wall 1006 over the apertures 1012 to expel the adhesive 1060 through the apertures 1012.

In some embodiments, the movement of the first rib 1017a and the second rib 1017b can be selectively decoupled to control a volume of the chamber region between the ribs 1017. For example, the ribs 1017 can be carried by separate shafts that can rotate relative to one another to control a circumferential distance between the ribs 1017 and/or the intermediate wall of the plunger can be compressible to allow the circumferential distance between the ribs 1017 to change. In some embodiments, the housing 1002 can include a stop 1018 that is configured to limit movement of the first rib 1017a or the second rib 1017b through the second lumen 1010 (depending on the direction along which the actuator 1001 is rotated). The actuator 1001 can be configured to rotate freely relative to the housing 1002 until the first rib 1017a or the second rib 1017b engages the stop 1018. The movement of the ribs 1017 can then decouple so that the rib engaged with the stop 1018 remains stationary while the other one of the ribs 1017 continues moving circumferentially through the second lumen 1010, thus decreasing the volume of the chamber region between the ribs 1017 and increasing a pressure within the chamber region. Still, in some embodiments the housing 1002 does not include the stop 1018.

As previously noted, any of the adhesive delivery devices disclosed herein can be preloaded such that the adhesive is positioned within the second lumen of the housing as the device is advanced into the patient's tissue. It may be advantageous to prevent or limit inadvertent delivery of adhesive through the apertures of the housing prior to the intended delivery of the adhesive. In some embodiments, as previously described, the actuator can be configured to retain the adhesive within a chamber region that is separated from and/or misaligned with the apertures in a pre-delivery configuration to prevent inadvertent adhesive delivery. Additionally or alternatively, an adhesive delivery device of the present technology can include packaging configured to prevent or limit inadvertent delivery of adhesive from the device. As but one example, the adhesive delivery device can include a covering positioned on an outer surface of the outer wall of the housing of the device over the apertures to physically block the adhesive from moving beyond the outer wall. The covering can be configured to be removed prior to insertion of the housing into the patient's tissue. Alternatively, the covering can be configured to be removed after insertion of the housing into the patient's tissue. For example, the covering can be slidable over the housing and/or can be split along its length to facilitate removal of the covering from the housing.

CONCLUSION

Although many of the embodiments are described above with respect to systems, devices, and methods for delivering material to extravascular spaces proximate vessel wall openings, the technology is applicable to other applications and/or other approaches, such as delivering material to other wounds or anatomical regions. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-10B.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art. The term "at least partially" includes both a partial and complete relationship between the parts being described. For example, in the phrase "the outer wall at least partially circumferentially surrounds the inner wall," means the outer wall may surround only a portion of the circumference of the inner wall, or may surround the entirety of the circumference of the inner wall.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A device for delivering a medical adhesive to a subcutaneous region proximate and extravascular to an opening in a wall of a blood vessel, the device comprising:
   a housing comprising a proximal end and a distal end opposite the proximal end along a longitudinal dimension of the housing, the housing comprising:
      an inner wall and an outer wall extending along the longitudinal dimension of the housing, the outer wall radially spaced apart from and circumferentially surrounding the inner wall, wherein:
      the inner wall defines a first lumen extending from the proximal end of the housing to the distal end of the housing along the longitudinal dimension of the housing, the first lumen being open at the proximal and distal ends of the housing, wherein the first lumen is configured to receive an elongate member therein;
      a second lumen defined between the outer wall and the inner wall such that the second lumen at least partially circumferentially surrounds the first lumen and extends from the proximal end of the housing towards the distal end of the housing along the longitudinal dimension of the housing, the second lumen being open at the proximal end of the housing; and
      the outer wall defines an aperture extending radially through the outer wall from the second lumen to an environment external of the housing such that the aperture fluidically couples the second lumen to the environment external of the housing;
   a medical adhesive positioned within the second lumen of the housing; and
   an actuator configured to be slidably received within the second lumen, wherein movement of the actuator within the second lumen forces the medical adhesive to move through the aperture to the environment external of the housing.

2. The device of claim 1, wherein the actuator comprises a proximal end and a distal end opposite the proximal end along a longitudinal dimension of the actuator, the actuator comprising a sidewall defining a channel extending longitudinally from the proximal end of the actuator to the distal end of the actuator, wherein the channel is open at the proximal and distal ends of the actuator and is configured to receive the elongate member therein.

3. The device of claim 2, wherein, when the actuator is positioned within the second lumen, the channel at least partially circumferentially surrounds the first lumen.

4. The device of claim 1, wherein at least a distal end of the actuator has an outer diameter at least as large as an outer diameter of the second lumen.

5. The device of claim 1, wherein the second lumen is closed at the distal end of the housing.

6. The device of claim 1, wherein distal advancement of the actuator relative to the housing forces the medical adhesive to move through the aperture to the environment external of the housing.

7. The device of claim 1, wherein proximal retraction of the actuator relative to the housing forces the medical adhesive to move through the aperture to the environment external of the housing.

8. The device of claim 1, wherein sliding the actuator longitudinally relative to the housing forces the medical adhesive to longitudinally align with and move through the aperture to the environment external of the housing.

9. The device of claim 1, wherein the actuator includes a shaft and a plunger distal of the shaft, the plunger having a proximal flange, a distal flange opposite the proximal flange along a longitudinal dimension of the plunger, and an intermediate wall therebetween, and wherein the proximal and distal flanges each have an outer diameter at least as large as an outer diameter of the second lumen and the intermediate wall has an outer diameter less than the outer diameter of the proximal and distal flanges.

10. The device of claim 9, wherein the proximal and distal flanges and the intermediate wall of the actuator define a chamber region, and wherein, when the actuator is positioned within the second lumen, the medical adhesive is positioned within the chamber region within the second lumen radially between the intermediate wall and the housing.

11. The device of claim 10, wherein the actuator comprises a rib extending longitudinally within the chamber region such that, when the actuator is positioned within the second lumen, the rib extends radially from the intermediate wall of the actuator to the housing.

12. The device of claim 11, wherein rotation of the actuator relative to the housing causes the rib to force the medical adhesive to move circumferentially through the second lumen and radially through the aperture to the environment external of the housing.

13. The device of claim 12, wherein rotating the actuator relative to the housing causes the rib to force the medical adhesive to circumferentially align with the aperture.

14. The device of claim 11, wherein the rib is a first rib, the actuator further comprising a second rib extending longitudinally within the chamber region, the second rib being circumferentially spaced apart from the first rib.

15. The device of claim 14, wherein, when the actuator is positioned within the second lumen, the medical adhesive is located circumferentially between the first and second ribs.

16. The device of claim 15, wherein rotating the actuator relative to the housing causes at least one of the first rib or the second rib to force the medical adhesive to circumferentially align with the aperture.

17. The device of claim 1, wherein the outer wall of the housing defines a plurality of apertures.

18. The device of claim 17, wherein at least some of the apertures are at least partially longitudinally aligned.

19. The device of claim 17, wherein at least some of the apertures are at least partially circumferentially aligned.

20. The device of claim 1, wherein the outer wall of the housing tapers in a distal direction.

\*   \*   \*   \*   \*